(12) United States Patent
Reggiardo

(10) Patent No.: US 7,679,407 B2
(45) Date of Patent: Mar. 16, 2010

(54) METHOD AND APPARATUS FOR PROVIDING PEAK DETECTION CIRCUITRY FOR DATA COMMUNICATION SYSTEMS

(75) Inventor: Christopher V. Reggiardo, Castro Valley, CA (US)

(73) Assignee: Abbott Diabetes Care Inc., Alameda, CA (US)

( * ) Notice: Subject to any disclaimer, the term of this patent is extended or adjusted under 35 U.S.C. 154(b) by 0 days.

(21) Appl. No.: 10/832,512

(22) Filed: Apr. 27, 2004

(65) Prior Publication Data

US 2009/0083003 A1    Mar. 26, 2009

Related U.S. Application Data

(60) Provisional application No. 60/466,243, filed on Apr. 28, 2003.

(51) Int. Cl.
*H03K 5/153* (2006.01)

(52) U.S. Cl. .......................................... 327/58; 327/61

(58) Field of Classification Search ............ 327/58, 327/194–195, 531–533, 580, 584, 586, 558, 327/61

See application file for complete search history.

(56) References Cited

U.S. PATENT DOCUMENTS

| | | | |
|---|---|---|---|
| 2,915,579 A | 12/1959 | Mendelsohn | |
| 3,750,687 A | 8/1973 | Williams | |
| 3,843,455 A | 10/1974 | Bier | |
| 3,930,493 A | 1/1976 | Williamson | |
| 3,994,799 A | 11/1976 | Yao et al. | |
| 4,018,547 A | 4/1977 | Rogen | |
| 4,121,282 A * | 10/1978 | Ohsawa | 363/21.08 |
| 4,193,397 A | 3/1980 | Tucker et al. | |
| 4,268,173 A | 5/1981 | Barnard et al. | |
| 4,401,122 A | 8/1983 | Clark, Jr. | |
| 4,439,197 A | 3/1984 | Honda et al. | |
| 4,447,224 A | 5/1984 | DeCant, Jr. et al. | |
| 4,458,686 A | 7/1984 | Clark, Jr. | |
| 4,467,811 A | 8/1984 | Clark, Jr. | |

(Continued)

FOREIGN PATENT DOCUMENTS

EP    0455455    11/1991

(Continued)

OTHER PUBLICATIONS

Barbosa, R. M., et al., "Electrochemical Studies of Zinc in Zinc-Insulin Solution", *Journal of the Royal Society of Chemistry, Analyst*, vol. 121, No. 12, 1996, pp. 1789-1793.

(Continued)

*Primary Examiner*—Lincoln Donovan
*Assistant Examiner*—Thomas J Hiltunen
(74) *Attorney, Agent, or Firm*—Jackson & Co., LLP

(57) ABSTRACT

Method and apparatus for providing a peak detection circuit comprising a diode including an input terminal and an output terminal the input terminal of the diode configured to receive an input signal, a capacitor operatively coupled to the output terminal of the diode, an output terminal operatively coupled to the capacitor and the output terminal of the diode for outputting an output signal is provided. Other equivalent switching configuration is further provided to effectively detect and compensate for a voltage droop from a power supply signal, as well as to electrically isolate the voltage droop from the system circuitry.

27 Claims, 6 Drawing Sheets

U.S. PATENT DOCUMENTS

| | | | |
|---|---|---|---|
| 4,494,950 A | 1/1985 | Fischell | |
| 4,512,348 A | 4/1985 | Uchigaki et al. | |
| 4,531,235 A * | 7/1985 | Brusen | 455/273 |
| 4,563,249 A | 1/1986 | Hale | |
| 4,570,492 A | 2/1986 | Walsh | |
| 4,633,878 A | 1/1987 | Bombardieri | |
| 4,686,624 A | 8/1987 | Blum et al. | |
| 4,850,959 A | 7/1989 | Findl | |
| 4,851,827 A | 7/1989 | Nicholas | |
| 4,866,396 A * | 9/1989 | Tamura | 329/352 |
| 4,890,621 A | 1/1990 | Hakky | |
| 4,953,552 A | 9/1990 | DeMarzo | |
| 4,979,509 A | 12/1990 | Hakky | |
| 4,984,581 A | 1/1991 | Stice | |
| 5,004,532 A | 4/1991 | Hale et al. | |
| 5,012,667 A | 5/1991 | Kruse | |
| 5,019,974 A | 5/1991 | Beckers | |
| 5,036,861 A | 8/1991 | Sembrowich et al. | |
| 5,051,880 A * | 9/1991 | Harm et al. | 363/49 |
| 5,079,920 A | 1/1992 | Whitehead et al. | |
| 5,081,421 A | 1/1992 | Miller et al. | |
| 5,101,814 A | 4/1992 | Palti | |
| 5,124,661 A | 6/1992 | Zelin et al. | |
| 5,139,023 A | 8/1992 | Stanley et al. | |
| 5,190,041 A | 3/1993 | Palti | |
| 5,207,666 A | 5/1993 | Idriss et al. | |
| 5,211,371 A | 5/1993 | Coffee | |
| 5,211,626 A | 5/1993 | Frank et al. | |
| 5,262,305 A | 11/1993 | Heller et al. | |
| 5,278,997 A | 1/1994 | Martin | |
| 5,291,887 A | 3/1994 | Stanley et al. | |
| 5,324,599 A | 6/1994 | Oyama et al. | |
| 5,325,280 A | 6/1994 | Tortola et al. | |
| 5,356,786 A | 10/1994 | Heller et al. | |
| 5,366,292 A | 11/1994 | Voss | |
| 5,368,028 A | 11/1994 | Palti | |
| 5,371,687 A | 12/1994 | Holmes, II et al. | |
| 5,372,133 A | 12/1994 | Hogen Esch | |
| 5,376,070 A | 12/1994 | Purvis et al. | |
| 5,391,250 A | 2/1995 | Cheney, II et al. | |
| 5,398,681 A | 3/1995 | Kupershmidt | |
| 5,404,585 A | 4/1995 | Vimpari et al. | |
| 5,406,301 A | 4/1995 | Ravid | |
| 5,445,611 A | 8/1995 | Eppstein et al. | |
| 5,448,992 A | 9/1995 | Kupershmidt | |
| 5,458,140 A | 10/1995 | Eppstein et al. | |
| 5,469,025 A | 11/1995 | Kanemori et al. | |
| 5,494,562 A | 2/1996 | Maley et al. | |
| 5,497,772 A | 3/1996 | Schulman et al. | |
| 5,507,288 A | 4/1996 | Bocker et al. | |
| 5,517,434 A | 5/1996 | Hanson et al. | |
| 5,559,528 A | 9/1996 | Ravid | |
| 5,568,400 A * | 10/1996 | Stark et al. | 702/85 |
| 5,575,770 A | 11/1996 | Melsky et al. | |
| 5,593,852 A | 1/1997 | Heller et al. | |
| 5,594,906 A | 1/1997 | Holmes, II et al. | |
| 5,604,404 A * | 2/1997 | Sahara | 315/8 |
| 5,615,671 A | 4/1997 | Schoonen et al. | |
| 5,622,413 A | 4/1997 | Kim et al. | |
| 5,622,482 A | 4/1997 | Lee | |
| 5,640,954 A | 6/1997 | Pfeiffer et al. | |
| 5,645,709 A | 7/1997 | Birch et al. | |
| 5,660,163 A | 8/1997 | Schulman et al. | |
| 5,661,643 A * | 8/1997 | Blakely et al. | 363/21.16 |
| 5,662,461 A | 9/1997 | Ono | |
| 5,671,301 A | 9/1997 | Kupershmidt | |
| 5,695,949 A | 12/1997 | Galen et al. | |
| 5,703,928 A | 12/1997 | Galloway et al. | |
| 5,707,502 A | 1/1998 | McCaffrey et al. | |
| 5,708,247 A | 1/1998 | McAleer et al. | |
| 5,711,861 A | 1/1998 | Ward et al. | |
| 5,711,868 A | 1/1998 | Maley et al. | |
| 5,722,397 A | 3/1998 | Eppstein | |
| 5,741,211 A | 4/1998 | Reririe et al. | |
| 5,748,872 A | 5/1998 | Norman | |
| 5,759,510 A | 6/1998 | Pillai | |
| 5,771,890 A | 6/1998 | Tamada | |
| 5,774,254 A | 6/1998 | Berlin | |
| 5,786,439 A | 7/1998 | Van Antwerp et al. | |
| 5,790,297 A | 8/1998 | Berlin | |
| 5,791,344 A | 8/1998 | Schulman et al. | |
| 5,814,599 A | 9/1998 | Mitragotri et al. | |
| 5,815,303 A | 9/1998 | Berlin | |
| 5,822,715 A | 10/1998 | Worthington et al. | |
| 5,825,488 A | 10/1998 | Kohl et al. | |
| 5,848,990 A | 12/1998 | Cirelli et al. | |
| 5,873,026 A | 2/1999 | Reames | |
| 5,885,211 A | 3/1999 | Eppstein et al. | |
| 5,899,855 A | 5/1999 | Brown | |
| 5,913,833 A | 6/1999 | Elstrom et al. | |
| 5,923,512 A | 7/1999 | Brownlow et al. | |
| 5,947,921 A | 9/1999 | Johnson et al. | |
| 5,948,512 A | 9/1999 | Kubota et al. | |
| 5,951,836 A | 9/1999 | McAleer et al. | |
| 5,954,643 A | 9/1999 | Van Antwerp et al. | |
| 5,965,380 A | 10/1999 | Heller et al. | |
| 5,971,922 A | 10/1999 | Arita et al. | |
| 6,001,067 A | 12/1999 | Shults et al. | |
| 6,002,961 A | 12/1999 | Mitragotri et al. | |
| 6,011,486 A | 1/2000 | Casey | |
| 6,014,577 A | 1/2000 | Henning et al. | |
| 6,018,678 A | 1/2000 | Mitragotri et al. | |
| 6,023,629 A | 2/2000 | Tamada | |
| 6,024,539 A | 2/2000 | Blomquist et al. | |
| 6,026,320 A | 2/2000 | Carlson et al. | |
| 6,027,459 A | 2/2000 | Shain et al. | |
| 6,027,496 A | 2/2000 | Loomis et al. | |
| 6,027,692 A | 2/2000 | Galen et al. | |
| 6,032,059 A | 2/2000 | Henning et al. | |
| 6,041,253 A | 3/2000 | Kost et al. | |
| 6,041,665 A | 3/2000 | Hussain | |
| 6,059,546 A | 5/2000 | Brenan et al. | |
| 6,063,039 A | 5/2000 | Cunningham et al. | |
| 6,064,368 A | 5/2000 | Kang | |
| 6,066,243 A | 5/2000 | Anderson et al. | |
| 6,067,017 A | 5/2000 | Stewart et al. | |
| 6,067,463 A | 5/2000 | Jeng et al. | |
| 6,071,249 A | 6/2000 | Cunningham et al. | |
| 6,071,251 A | 6/2000 | Cunningham et al. | |
| 6,073,031 A | 6/2000 | Helstab et al. | |
| 6,077,660 A | 6/2000 | Wong et al. | |
| 6,081,104 A * | 6/2000 | Kern | 323/268 |
| 6,083,710 A | 7/2000 | Heller et al. | |
| 6,085,871 A | 7/2000 | Karamata | |
| 6,091,975 A | 7/2000 | Daddona et al. | |
| 6,093,156 A | 7/2000 | Cunningham et al. | |
| 6,121,009 A | 9/2000 | Heller et al. | |
| 6,129,823 A | 10/2000 | Hughes et al. | |
| 6,132,371 A * | 10/2000 | Dempsey et al. | 600/300 |
| 6,142,939 A | 11/2000 | Eppstein et al. | |
| 6,144,303 A | 11/2000 | Federman | |
| 6,144,869 A | 11/2000 | Berner et al. | |
| 6,144,922 A | 11/2000 | Douglas et al. | |
| 6,154,855 A | 11/2000 | Norman | |
| 6,155,992 A | 12/2000 | Henning et al. | |
| 6,157,442 A | 12/2000 | Raskas | |
| 6,160,449 A * | 12/2000 | Klomsdorf et al. | 330/149 |
| 6,162,202 A | 12/2000 | Sicurelli et al. | |
| 6,162,611 A | 12/2000 | Heller et al. | |
| 6,164,284 A | 12/2000 | Schulman et al. | |
| 6,173,160 B1 * | 1/2001 | Liimatainen | 455/67.11 |
| 6,175,752 B1 | 1/2001 | Say et al. | |
| 6,180,416 B1 | 1/2001 | Kurnik et al. | |
| 6,185,452 B1 | 2/2001 | Schulman et al. | |

| | | |
|---|---|---|
| 6,201,980 B1 | 3/2001 | Darrow et al. |
| 6,206,841 B1 | 3/2001 | Cunningham et al. |
| 6,208,894 B1 | 3/2001 | Schulman et al. |
| 6,212,416 B1 | 4/2001 | Ward et al. |
| 6,222,514 B1 | 4/2001 | DeLuca |
| 6,232,370 B1 | 5/2001 | Kubota et al. |
| 6,233,471 B1 | 5/2001 | Berner et al. |
| 6,242,961 B1 * | 6/2001 | Liu et al. .................... 327/307 |
| 6,245,060 B1 | 6/2001 | Loomis et al. |
| 6,248,067 B1 | 6/2001 | Causey, III et al. |
| 6,262,708 B1 | 7/2001 | Chu |
| 6,272,364 B1 | 8/2001 | Kurnik |
| 6,278,425 B1 | 8/2001 | DeLuca |
| 6,280,587 B1 | 8/2001 | Matsumoto |
| 6,283,926 B1 | 9/2001 | Cunningham et al. |
| 6,284,478 B1 | 9/2001 | Heller et al. |
| 6,295,506 B1 | 9/2001 | Heinonen et al. |
| 6,298,254 B2 | 10/2001 | Tamada |
| 6,298,255 B1 | 10/2001 | Cordero et al. |
| 6,299,578 B1 | 10/2001 | Kurnik et al. |
| 6,301,499 B1 | 10/2001 | Carlson et al. |
| 6,306,104 B1 | 10/2001 | Cunningham et al. |
| 6,309,351 B1 | 10/2001 | Kurnik et al. |
| 6,312,888 B1 | 11/2001 | Wong et al. |
| 6,315,721 B2 | 11/2001 | Schulman et al. |
| 6,326,160 B1 | 12/2001 | Dunn et al. |
| 6,329,161 B1 | 12/2001 | Heller et al. |
| 6,341,232 B1 | 1/2002 | Conn et al. |
| 6,356,776 B1 | 3/2002 | Berner et al. |
| 6,360,888 B1 | 3/2002 | McIvor et al. |
| 6,366,793 B1 | 4/2002 | Bell et al. |
| 6,368,141 B1 | 4/2002 | VanAntwerp et al. |
| 6,368,274 B1 | 4/2002 | Van Antwerp et al. |
| 6,372,371 B1 | 4/2002 | Iarochenko et al. |
| 6,375,344 B1 | 4/2002 | Hanson et al. |
| 6,375,638 B2 | 4/2002 | Nason et al. |
| 6,377,894 B1 | 4/2002 | Deweese et al. |
| 6,381,496 B1 | 4/2002 | Meadows et al. |
| 6,393,318 B1 | 5/2002 | Conn et al. |
| 6,403,944 B1 | 6/2002 | MacKenzie et al. |
| 6,405,066 B1 | 6/2002 | Essenpreis et al. |
| 6,408,402 B1 | 6/2002 | Norman |
| 6,417,074 B2 | 7/2002 | Kopley et al. |
| 6,419,642 B1 | 7/2002 | Marchitto et al. |
| 6,425,829 B1 | 7/2002 | Julien |
| 6,427,088 B1 | 7/2002 | Bowman, IV et al. |
| 6,432,585 B1 | 8/2002 | Kawakami et al. |
| 6,437,379 B2 | 8/2002 | Kopley et al. |
| 6,438,385 B1 | 8/2002 | Heinonen et al. |
| 6,438,414 B1 | 8/2002 | Conn et al. |
| 6,442,413 B1 | 8/2002 | Silver |
| 6,462,162 B2 | 10/2002 | Van Antwerp et al. |
| 6,464,848 B1 | 10/2002 | Matsumoto |
| 6,466,807 B1 | 10/2002 | Dobson et al. |
| 6,466,810 B1 | 10/2002 | Ward et al. |
| 6,468,222 B1 | 10/2002 | Mault et al. |
| 6,471,980 B2 | 10/2002 | Sirhan et al. |
| 6,472,991 B1 | 10/2002 | Schulman et al. |
| 6,478,736 B1 | 11/2002 | Mault |
| 6,480,730 B2 | 11/2002 | Darrow et al. |
| 6,482,158 B2 | 11/2002 | Mault |
| 6,485,138 B1 | 11/2002 | Kubota et al. |
| 6,492,180 B2 | 12/2002 | Brown et al. |
| 6,506,168 B1 | 1/2003 | Fathallah et al. |
| 6,513,532 B2 | 2/2003 | Mault et al. |
| 6,514,460 B1 | 2/2003 | Fendrock |
| 6,514,689 B2 | 2/2003 | Han et al. |
| 6,514,718 B2 | 2/2003 | Heller et al. |
| 6,522,530 B2 * | 2/2003 | Bang .................... 361/681 |
| 6,525,330 B2 | 2/2003 | Paolini et al. |
| 6,526,298 B1 | 2/2003 | Khalil et al. |
| 6,529,772 B2 | 3/2003 | Carlson et al. |
| 6,530,915 B1 | 3/2003 | Eppstein et al. |
| 6,535,753 B1 | 3/2003 | Raskas |
| 6,537,243 B1 | 3/2003 | Henning et al. |
| 6,540,675 B2 | 4/2003 | Aceti et al. |
| 6,540,891 B1 | 4/2003 | Stewart et al. |
| 6,544,212 B2 | 4/2003 | Galley et al. |
| 6,546,269 B1 | 4/2003 | Kurnik |
| 6,549,796 B2 | 4/2003 | Sohrab |
| 6,551,276 B1 | 4/2003 | Mann et al. |
| 6,554,798 B1 | 4/2003 | Mann et al. |
| 6,558,320 B1 | 5/2003 | Causey et al. |
| 6,558,321 B1 | 5/2003 | Burd et al. |
| 6,558,351 B1 | 5/2003 | Steil et al. |
| 6,560,471 B1 * | 5/2003 | Heller et al. .................... 600/347 |
| 6,561,978 B1 | 5/2003 | Conn et al. |
| 6,562,001 B2 | 5/2003 | Lebel et al. |
| 6,564,105 B2 | 5/2003 | Starkweather et al. |
| 6,564,807 B1 | 5/2003 | Schulman et al. |
| 6,565,509 B1 | 5/2003 | Say et al. |
| 6,565,738 B1 | 5/2003 | Henning et al. |
| 6,569,157 B1 | 5/2003 | Shain et al. |
| 6,571,128 B2 | 5/2003 | Lebel et al. |
| 6,571,200 B1 | 5/2003 | Mault |
| 6,576,117 B1 | 6/2003 | Iketaki et al. |
| 6,577,899 B2 | 6/2003 | Lebel et al. |
| 6,579,498 B1 | 6/2003 | Eglise |
| 6,579,690 B1 | 6/2003 | Bonnecaze et al. |
| 6,582,393 B2 | 6/2003 | Sage, Jr. |
| 6,585,644 B2 | 7/2003 | Lebel et al. |
| 6,586,971 B1 * | 7/2003 | Naffziger et al. .................... 327/41 |
| 6,587,705 B1 | 7/2003 | Berner et al. |
| 6,589,229 B1 | 7/2003 | Connelly et al. |
| 6,594,514 B2 | 7/2003 | Berner et al. |
| 6,595,919 B2 | 7/2003 | Berner et al. |
| 6,596,016 B1 | 7/2003 | Vreman et al. |
| 6,600,997 B2 | 7/2003 | Deweese et al. |
| 6,602,469 B1 | 8/2003 | Maus et al. |
| 6,610,012 B2 | 8/2003 | Mault |
| 6,612,306 B1 | 9/2003 | Mault |
| 6,615,061 B1 | 9/2003 | Khalil et al. |
| 6,615,074 B2 * | 9/2003 | Mickle et al. .................... 600/509 |
| 6,618,603 B2 | 9/2003 | Varalli et al. |
| 6,620,106 B2 | 9/2003 | Mault |
| 6,629,934 B2 | 10/2003 | Mault et al. |
| 6,633,772 B2 | 10/2003 | Ford et al. |
| 6,635,014 B2 | 10/2003 | Starkweather et al. |
| 6,641,533 B2 | 11/2003 | Causey et al. |
| 6,645,142 B2 | 11/2003 | Braig et al. |
| 6,648,821 B2 | 11/2003 | Lebel et al. |
| 6,650,064 B2 | 11/2003 | Guthrie et al. |
| 6,653,091 B1 | 11/2003 | Dunn et al. |
| 6,659,948 B2 | 12/2003 | Lebel et al. |
| 6,668,196 B1 | 12/2003 | Villegas et al. |
| 6,669,663 B1 | 12/2003 | Thompson |
| 6,669,669 B2 | 12/2003 | Flaherty et al. |
| 6,679,841 B2 | 1/2004 | Bojan et al. |
| 6,687,522 B2 | 2/2004 | Tamada |
| 6,687,546 B2 | 2/2004 | Lebel et al. |
| 6,692,457 B2 | 2/2004 | Flaherty |
| 6,694,191 B2 | 2/2004 | Lebel et al. |
| 6,695,885 B2 | 2/2004 | Schulman et al. |
| 6,702,857 B2 | 3/2004 | Brauker et al. |
| 6,723,072 B2 | 4/2004 | Flaherty et al. |
| 6,728,560 B2 | 4/2004 | Kollias et al. |
| 6,730,200 B1 | 5/2004 | Stewart et al. |
| 6,731,976 B2 | 5/2004 | Penn et al. |
| 6,733,446 B2 | 5/2004 | Lebel et al. |
| 6,736,777 B2 | 5/2004 | Kim et al. |
| 6,738,654 B2 | 5/2004 | Sohrab |
| 6,740,075 B2 | 5/2004 | Lebel et al. |
| 6,741,877 B1 | 5/2004 | Shults et al. |
| 6,743,635 B2 | 6/2004 | Neel et al. |
| 6,752,787 B1 | 6/2004 | Causey, III et al. |
| 6,758,810 B2 | 7/2004 | Lebel et al. |

| Patent | Date | Inventors |
|---|---|---|
| 6,764,581 B1 | 7/2004 | Forrow et al. |
| 6,768,425 B2 | 7/2004 | Flaherty et al. |
| 6,773,563 B2 | 8/2004 | Matsumoto |
| 6,790,178 B1 | 9/2004 | Mault et al. |
| 6,794,195 B2 | 9/2004 | Colvin, Jr. |
| 6,799,861 B2 | 10/2004 | Naghi et al. |
| 6,809,653 B1 | 10/2004 | Mann et al. |
| 6,810,290 B2 | 10/2004 | Lebel et al. |
| 6,811,533 B2 | 11/2004 | Lebel et al. |
| 6,811,534 B2 | 11/2004 | Bowman, IV et al. |
| 6,813,519 B2 | 11/2004 | Lebel et al. |
| 6,816,742 B2 | 11/2004 | Kim et al. |
| 6,818,348 B1 | 11/2004 | Venkatesan et al. |
| 6,832,114 B1 | 12/2004 | Whitehurst et al. |
| 6,833,540 B2 | 12/2004 | MacKenzie et al. |
| 6,835,553 B2 * | 12/2004 | Han et al. ................. 435/14 |
| 6,837,858 B2 | 1/2005 | Cunningham et al. |
| 6,839,596 B2 | 1/2005 | Nelson et al. |
| 6,840,912 B2 | 1/2005 | Kloepfer et al. |
| 6,849,237 B2 | 2/2005 | Housefield et al. |
| 6,850,790 B2 | 2/2005 | Berner et al. |
| 6,859,831 B1 | 2/2005 | Gelvin et al. |
| 6,862,465 B2 | 3/2005 | Shults et al. |
| 6,872,200 B2 | 3/2005 | Mann et al. |
| 6,873,268 B2 | 3/2005 | Lebel et al. |
| 6,881,551 B2 | 4/2005 | Heller et al. |
| 6,892,085 B2 | 5/2005 | McIvor et al. |
| 6,893,396 B2 | 5/2005 | Schulze et al. |
| 6,895,265 B2 | 5/2005 | Silver |
| 6,898,451 B2 | 5/2005 | Wuori |
| 6,899,683 B2 | 5/2005 | Mault et al. |
| 6,899,684 B2 | 5/2005 | Mault et al. |
| 6,904,301 B2 | 6/2005 | Raskas |
| 6,907,127 B1 | 6/2005 | Kravitz et al. |
| 6,908,535 B2 | 6/2005 | Rankin et al. |
| 6,916,159 B2 | 7/2005 | Rush et al. |
| 6,918,874 B1 | 7/2005 | Hatch et al. |
| 6,922,576 B2 | 7/2005 | Raskas |
| 6,922,578 B2 | 7/2005 | Eppstein et al. |
| 6,923,764 B2 | 8/2005 | Aceti et al. |
| 6,931,327 B2 | 8/2005 | Goode, Jr. et al. |
| 6,936,029 B2 | 8/2005 | Mann et al. |
| 6,949,816 B2 | 9/2005 | Brown et al. |
| 6,950,708 B2 | 9/2005 | Bowman IV et al. |
| 6,952,603 B2 | 10/2005 | Gerber et al. |
| 6,955,650 B2 | 10/2005 | Mault et al. |
| 6,958,129 B2 | 10/2005 | Galen et al. |
| 6,958,705 B2 | 10/2005 | Lebel et al. |
| 6,974,437 B2 | 12/2005 | Lebel et al. |
| 6,979,326 B2 | 12/2005 | Mann et al. |
| 6,990,366 B2 | 1/2006 | Say et al. |
| 6,990,372 B2 | 1/2006 | Perron et al. |
| 6,997,911 B2 | 2/2006 | Klitmose |
| 6,997,920 B2 | 2/2006 | Mann et al. |
| 6,999,810 B2 | 2/2006 | Berner et al. |
| 7,003,340 B2 | 2/2006 | Say et al. |
| 7,003,341 B2 | 2/2006 | Say et al. |
| 7,005,857 B2 | 2/2006 | Stiene et al. |
| 7,006,858 B2 | 2/2006 | Silver et al. |
| 7,010,356 B2 | 3/2006 | Jog et al. |
| 7,011,630 B2 | 3/2006 | Desai et al. |
| 7,020,508 B2 | 3/2006 | Stiroric et al. |
| 7,024,245 B2 | 4/2006 | Lebel et al. |
| 7,024,249 B2 | 4/2006 | Weisner et al. |
| 7,025,743 B2 | 4/2006 | Mann et al. |
| 7,029,444 B2 | 4/2006 | Shin et al. |
| 7,034,677 B2 | 4/2006 | Steinthal et al. |
| 7,041,468 B2 | 5/2006 | Drucker et al. |
| 7,043,287 B1 | 5/2006 | Khalil et al. |
| 7,067,498 B2 | 6/2006 | Wolf et al. |
| 7,070,591 B2 | 7/2006 | Adams et al. |
| 7,072,738 B2 | 7/2006 | Bonney et al. |
| 7,074,307 B2 | 7/2006 | Simpson et al. |
| 7,077,328 B2 | 7/2006 | Krishnaswamy et al. |
| 7,079,901 B1 | 7/2006 | Loftin et al. |
| 7,081,195 B2 | 7/2006 | Simpson et al. |
| 7,083,593 B2 | 8/2006 | Stultz |
| 7,086,277 B2 | 8/2006 | Tess et al. |
| 7,092,762 B1 | 8/2006 | Loftin et al. |
| 7,097,983 B2 | 8/2006 | Markovsky et al. |
| 7,098,803 B2 | 8/2006 | Mann et al. |
| 7,108,711 B2 | 9/2006 | Vogel et al. |
| 7,108,778 B2 | 9/2006 | Simpson et al. |
| 7,110,803 B2 | 9/2006 | Shults et al. |
| 7,114,502 B2 | 10/2006 | Schulman et al. |
| 7,123,206 B2 | 10/2006 | Hess et al. |
| 7,133,710 B2 | 11/2006 | Acosta et al. |
| 7,134,999 B2 | 11/2006 | Brauker et al. |
| 7,136,689 B2 | 11/2006 | Shults et al. |
| 7,136,704 B2 | 11/2006 | Schulman |
| 7,149,581 B2 | 12/2006 | Goedeke |
| 7,153,212 B1 | 12/2006 | Karten et al. |
| 7,154,398 B2 | 12/2006 | Chen et al. |
| 7,163,511 B2 | 1/2007 | Conn et al. |
| 7,171,274 B2 | 1/2007 | Starkweather et al. |
| 7,181,261 B2 | 2/2007 | Silver et al. |
| 7,186,566 B2 | 3/2007 | Qian |
| 7,186,791 B2 | 3/2007 | Bruno et al. |
| 7,192,450 B2 | 3/2007 | Brauker et al. |
| 7,198,603 B2 | 4/2007 | Penner et al. |
| 7,202,734 B1 | 4/2007 | Raab |
| 7,205,409 B2 | 4/2007 | Pei et al. |
| 7,208,119 B1 | 4/2007 | Kurtock et al. |
| 7,211,048 B1 | 5/2007 | Najafi et al. |
| 7,225,535 B2 | 6/2007 | Feldman et al. |
| 7,226,442 B2 | 6/2007 | Sheppard, Jr. et al. |
| 7,226,978 B2 | 6/2007 | Tapsak et al. |
| 7,258,666 B2 | 8/2007 | Brown |
| 7,266,400 B2 | 9/2007 | Fine et al. |
| 7,276,029 B2 | 10/2007 | Goode, Jr. et al. |
| 7,283,867 B2 | 10/2007 | Strother et al. |
| 7,299,080 B2 | 11/2007 | Acosta et al. |
| 7,310,544 B2 | 12/2007 | Brister et al. |
| 7,323,091 B1 | 1/2008 | Gillette et al. |
| 7,324,949 B2 | 1/2008 | Bristol et al. |
| 7,364,592 B2 | 4/2008 | Carr-Brendel et al. |
| 7,366,556 B2 | 4/2008 | Brister et al. |
| 7,379,765 B2 | 5/2008 | Petisce et al. |
| 7,424,318 B2 | 9/2008 | Brister et al. |
| 7,460,898 B2 | 12/2008 | Brister, et al. |
| 7,467,003 B2 | 12/2008 | Brister et al. |
| 7,471,972 B2 | 12/2008 | Rhodes et al. |
| 7,480,138 B2 | 1/2009 | Kogan et al. |
| 7,494,465 B2 | 2/2009 | Brister et al. |
| 7,497,827 B2 | 3/2009 | Brister et al. |
| 7,510,526 B2 | 3/2009 | Merry et al. |
| 7,519,408 B2 | 4/2009 | Rasdal et al. |
| 7,583,990 B2 | 9/2009 | Goode, Jr. et al. |
| 7,591,801 B2 | 9/2009 | Brauker et al. |
| 7,599,726 B2 | 10/2009 | Goode, Jr. et al. |
| 7,602,310 B2 | 10/2009 | Mann et al. |
| 7,613,491 B2 | 11/2009 | Boock et al. |
| 7,615,007 B2 | 11/2009 | Shults et al. |
| 7,632,228 B2 | 12/2009 | Brauker et al. |
| 2001/0016682 A1 | 8/2001 | Berner et al. |
| 2001/0016683 A1 | 8/2001 | Darrow et al. |
| 2001/0020124 A1 | 9/2001 | Tamada |
| 2001/0023095 A1 | 9/2001 | Kopley et al. |
| 2001/0024864 A1 | 9/2001 | Kopley et al. |
| 2001/0029340 A1 | 10/2001 | Mault et al. |
| 2001/0037060 A1 | 11/2001 | Thompson et al. |
| 2001/0037069 A1 | 11/2001 | Carlson et al. |
| 2001/0041830 A1 | 11/2001 | Varalli et al. |
| 2001/0044581 A1 | 11/2001 | Mault |
| 2001/0044588 A1 | 11/2001 | Mault |
| 2001/0049470 A1 | 12/2001 | Mault et al. |

| | | |
|---|---|---|
| 2001/0056255 A1 | 12/2001 | Kost et al. |
| 2002/0002326 A1 | 1/2002 | Causey, III et al. |
| 2002/0002328 A1 | 1/2002 | Tamada |
| 2002/0004640 A1 | 1/2002 | Conn et al. |
| 2002/0010414 A1 | 1/2002 | Coston et al. |
| 2002/0019022 A1 | 2/2002 | Dunn et al. |
| 2002/0026937 A1 | 3/2002 | Mault |
| 2002/0027164 A1 | 3/2002 | Mault et al. |
| 2002/0028995 A1 | 3/2002 | Mault |
| 2002/0040208 A1 | 4/2002 | Flaherty et al. |
| 2002/0042090 A1 | 4/2002 | Heller et al. |
| 2002/0047867 A1 | 4/2002 | Mault et al. |
| 2002/0053637 A1 | 5/2002 | Conn et al. |
| 2002/0062069 A1 | 5/2002 | Mault |
| 2002/0068858 A1 | 6/2002 | Braig et al. |
| 2002/0077765 A1 | 6/2002 | Mault |
| 2002/0077766 A1 | 6/2002 | Mault |
| 2002/0087056 A1 | 7/2002 | Aceti et al. |
| 2002/0091312 A1 | 7/2002 | Berner et al. |
| 2002/0091454 A1 | 7/2002 | Vasko |
| 2002/0103425 A1 | 8/2002 | Mault |
| 2002/0107433 A1 | 8/2002 | Mault |
| 2002/0107476 A1 | 8/2002 | Mann et al. |
| 2002/0109600 A1 | 8/2002 | Mault et al. |
| 2002/0118090 A1 | 8/2002 | Park et al. |
| 2002/0119711 A1 | 8/2002 | Van Antwerp et al. |
| 2002/0124017 A1 | 9/2002 | Mault |
| 2002/0133378 A1 | 9/2002 | Mault et al. |
| 2002/0161286 A1 | 10/2002 | Gerber et al. |
| 2002/0169394 A1 | 11/2002 | Eppstein et al. |
| 2002/0177764 A1 | 11/2002 | Sohrab |
| 2002/0193679 A1 | 12/2002 | Malave et al. |
| 2003/0023182 A1 | 1/2003 | Mault et al. |
| 2003/0023317 A1 | 1/2003 | Brauker et al. |
| 2003/0028089 A1 | 2/2003 | Galley et al. |
| 2003/0028120 A1 | 2/2003 | Mault et al. |
| 2003/0032868 A1 | 2/2003 | Graskov et al. |
| 2003/0032874 A1 | 2/2003 | Rhodes et al. |
| 2003/0040683 A1 | 2/2003 | Rule et al. |
| 2003/0050546 A1 | 3/2003 | Desai et al. |
| 2003/0060692 A1 | 3/2003 | Ruchti et al. |
| 2003/0060765 A1 | 3/2003 | Campbell et al. |
| 2003/0065257 A1 | 4/2003 | Mault et al. |
| 2003/0065273 A1 | 4/2003 | Mault et al. |
| 2003/0065274 A1 | 4/2003 | Mault et al. |
| 2003/0065275 A1 | 4/2003 | Mault et al. |
| 2003/0065308 A1 | 4/2003 | Lebel et al. |
| 2003/0078560 A1 | 4/2003 | Miller et al. |
| 2003/0100040 A1 | 5/2003 | Bonnacaze et al. |
| 2003/0100821 A1 | 5/2003 | Heller et al. |
| 2003/0105407 A1 | 6/2003 | Pearce, Jr. et al. |
| 2003/0107487 A1 | 6/2003 | Korman et al. |
| 2003/0108976 A1 | 6/2003 | Braig et al. |
| 2003/0130616 A1 | 7/2003 | Steil et al. |
| 2003/0134347 A1 | 7/2003 | Heller et al. |
| 2003/0135100 A1 | 7/2003 | Kim et al. |
| 2003/0135333 A1 | 7/2003 | Aceti et al. |
| 2003/0153820 A1 | 8/2003 | Berner et al. |
| 2003/0153821 A1 | 8/2003 | Berner et al. |
| 2003/0158472 A1 | 8/2003 | Sohrab |
| 2003/0158707 A1 | 8/2003 | Doi |
| 2003/0175806 A1 | 9/2003 | Rule et al. |
| 2003/0176933 A1 | 9/2003 | Lebel et al. |
| 2003/0181851 A1 | 9/2003 | Mann et al. |
| 2003/0181852 A1 | 9/2003 | Mann et al. |
| 2003/0187338 A1 | 10/2003 | Say et al. |
| 2003/0187525 A1 | 10/2003 | Mann et al. |
| 2003/0191376 A1 | 10/2003 | Samuels et al. |
| 2003/0191431 A1 | 10/2003 | Mann et al. |
| 2003/0195403 A1 | 10/2003 | Berner et al. |
| 2003/0195462 A1 | 10/2003 | Mann et al. |
| 2003/0198558 A1 | 10/2003 | Nason et al. |
| 2003/0208110 A1 | 11/2003 | Mault et al. |
| 2003/0208113 A1 | 11/2003 | Mault et al. |
| 2003/0208133 A1 | 11/2003 | Mault |
| 2003/0208409 A1 | 11/2003 | Mault |
| 2003/0212346 A1 | 11/2003 | Yuzhakov et al. |
| 2003/0212364 A1 | 11/2003 | Mann et al. |
| 2003/0212379 A1 | 11/2003 | Bylund et al. |
| 2003/0217966 A1 | 11/2003 | Tapsak et al. |
| 2003/0226695 A1 | 12/2003 | Mault |
| 2003/0232370 A1 | 12/2003 | Trifiro |
| 2003/0235817 A1 | 12/2003 | Bartkowiak et al. |
| 2004/0011671 A1 | 1/2004 | Shults et al. |
| 2004/0018486 A1 | 1/2004 | Dunn et al. |
| 2004/0019321 A1 | 1/2004 | Sage et al. |
| 2004/0027253 A1 | 2/2004 | Marsh et al. |
| 2004/0039256 A1 | 2/2004 | Kawatahara et al. |
| 2004/0045879 A1 | 3/2004 | Shults et al. |
| 2004/0054263 A1 | 3/2004 | Moerman et al. |
| 2004/0059201 A1 | 3/2004 | Ginsberg |
| 2004/0064133 A1 | 4/2004 | Miller et al. |
| 2004/0072357 A1 | 4/2004 | Stiene et al. |
| 2004/0073095 A1 | 4/2004 | Causey, III et al. |
| 2004/0085215 A1 | 5/2004 | Moberg et al. |
| 2004/0096959 A1 | 5/2004 | Stiene et al. |
| 2004/0100376 A1 | 5/2004 | Lye et al. |
| 2004/0106858 A1 | 6/2004 | Say et al. |
| 2004/0106859 A1 | 6/2004 | Say et al. |
| 2004/0106860 A1 | 6/2004 | Say et al. |
| 2004/0108226 A1 | 6/2004 | Polychronakos et al. |
| 2004/0115067 A1 | 6/2004 | Rush et al. |
| 2004/0122353 A1 | 6/2004 | Shahmirian et al. |
| 2004/0132220 A1* | 7/2004 | Fish .................... 436/525 |
| 2004/0133092 A1* | 7/2004 | Kain .................... 600/377 |
| 2004/0152622 A1 | 8/2004 | Keith et al. |
| 2004/0158137 A1 | 8/2004 | Eppstein et al. |
| 2004/0162473 A1 | 8/2004 | Sohrab |
| 2004/0164961 A1 | 8/2004 | Bal et al. |
| 2004/0167383 A1 | 8/2004 | Kim et al. |
| 2004/0167801 A1 | 8/2004 | Say et al. |
| 2004/0171921 A1 | 9/2004 | Say et al. |
| 2004/0176913 A1 | 9/2004 | Kawatahara et al. |
| 2004/0186362 A1 | 9/2004 | Brauker et al. |
| 2004/0186365 A1 | 9/2004 | Jin et al. |
| 2004/0193025 A1 | 9/2004 | Steil et al. |
| 2004/0193090 A1 | 9/2004 | Lebel et al. |
| 2004/0199059 A1 | 10/2004 | Brauker et al. |
| 2004/0202576 A1 | 10/2004 | Aceti et al. |
| 2004/0207054 A1 | 10/2004 | Brown et al. |
| 2004/0208780 A1 | 10/2004 | Faries, Jr. et al. |
| 2004/0210184 A1 | 10/2004 | Kost et al. |
| 2004/0225338 A1 | 11/2004 | Lebel et al. |
| 2004/0236200 A1 | 11/2004 | Say et al. |
| 2004/0248204 A1 | 12/2004 | Moerman |
| 2004/0249250 A1 | 12/2004 | McGee et al. |
| 2004/0249253 A1 | 12/2004 | Racchini et al. |
| 2004/0249254 A1 | 12/2004 | Racchini et al. |
| 2004/0249999 A1 | 12/2004 | Connolly et al. |
| 2004/0253736 A1 | 12/2004 | Stout et al. |
| 2004/0254429 A1 | 12/2004 | Yang |
| 2004/0254434 A1 | 12/2004 | Goodnow et al. |
| 2004/0263354 A1 | 12/2004 | Mann et al. |
| 2005/0003470 A1 | 1/2005 | Nelson et al. |
| 2005/0009126 A1 | 1/2005 | Andrews et al. |
| 2005/0010269 A1 | 1/2005 | Lebel et al. |
| 2005/0016276 A1 | 1/2005 | Guan et al. |
| 2005/0027179 A1 | 2/2005 | Berner et al. |
| 2005/0027180 A1 | 2/2005 | Goode, Jr. et al. |
| 2005/0027181 A1 | 2/2005 | Goode, Jr. et al. |
| 2005/0027462 A1 | 2/2005 | Goode, Jr. et al. |
| 2005/0027463 A1 | 2/2005 | Goode, Jr. et al. |
| 2005/0031689 A1 | 2/2005 | Shults et al. |
| 2005/0033132 A1 | 2/2005 | Shults et al. |
| 2005/0038680 A1 | 2/2005 | McMahon |
| 2005/0043598 A1 | 2/2005 | Goode, Jr. et al. |

| | | |
|---|---|---|
| 2005/0043894 A1 | 2/2005 | Fernandez |
| 2005/0045476 A1 | 3/2005 | Neel et al. |
| 2005/0049473 A1 | 3/2005 | Desai et al. |
| 2005/0051580 A1 | 3/2005 | Ramey |
| 2005/0053365 A1 | 3/2005 | Adams et al. |
| 2005/0054909 A1 | 3/2005 | Petisce et al. |
| 2005/0059926 A1 | 3/2005 | Sage, Jr. et al. |
| 2005/0065464 A1 | 3/2005 | Talbot et al. |
| 2005/0090607 A1 | 4/2005 | Tapsak et al. |
| 2005/0090808 A1 | 4/2005 | Malave et al. |
| 2005/0112169 A1 | 5/2005 | Brauker et al. |
| 2005/0113657 A1 | 5/2005 | Alarcon et al. |
| 2005/0113658 A1 | 5/2005 | Jacobson et al. |
| 2005/0118726 A1 | 6/2005 | Schultz et al. |
| 2005/0121322 A1 | 6/2005 | Say et al. |
| 2005/0124873 A1 | 6/2005 | Shults et al. |
| 2005/0137471 A1 | 6/2005 | Haar et al. |
| 2005/0143635 A1 | 6/2005 | Kamath et al. |
| 2005/0143636 A1 | 6/2005 | Zhang et al. |
| 2005/0148003 A1 | 7/2005 | Keith et al. |
| 2005/0154271 A1 | 7/2005 | Rasdal et al. |
| 2005/0161346 A1 | 7/2005 | Simpson et al. |
| 2005/0171503 A1 | 8/2005 | Van Den Berghe et al. |
| 2005/0171513 A1 | 8/2005 | Mann et al. |
| 2005/0173245 A1 | 8/2005 | Feldman et al. |
| 2005/0176136 A1 | 8/2005 | Burd et al. |
| 2005/0177036 A1 | 8/2005 | Shults et al. |
| 2005/0181012 A1 | 8/2005 | Saint et al. |
| 2005/0182306 A1 | 8/2005 | Sloan |
| 2005/0182451 A1 | 8/2005 | Griffin et al. |
| 2005/0187720 A1 | 8/2005 | Goode, Jr. et al. |
| 2005/0192557 A1 | 9/2005 | Brauker et al. |
| 2005/0195930 A1 | 9/2005 | Spital et al. |
| 2005/0199494 A1 | 9/2005 | Say et al. |
| 2005/0203360 A1 | 9/2005 | Brauker et al. |
| 2005/0214892 A1 | 9/2005 | Kovatchev et al. |
| 2005/0215871 A1 | 9/2005 | Feldman et al. |
| 2005/0215872 A1 | 9/2005 | Berner et al. |
| 2005/0235732 A1 | 10/2005 | Rush |
| 2005/0238503 A1 | 10/2005 | Rush et al. |
| 2005/0239154 A1 | 10/2005 | Feldman et al. |
| 2005/0245795 A1 | 11/2005 | Goode, Jr. et al. |
| 2005/0245799 A1 | 11/2005 | Brauker et al. |
| 2005/0249606 A1 | 11/2005 | Rush |
| 2005/0251083 A1 | 11/2005 | Carr-Brendel et al. |
| 2005/0261660 A1 | 11/2005 | Choi |
| 2005/0267780 A1 | 12/2005 | Ray et al. |
| 2005/0271546 A1 | 12/2005 | Gerber et al. |
| 2005/0271547 A1 | 12/2005 | Gerber et al. |
| 2005/0272640 A1 | 12/2005 | Doyle, III et al. |
| 2005/0272985 A1 | 12/2005 | Kotulla et al. |
| 2005/0277844 A1 | 12/2005 | Strother et al. |
| 2005/0287620 A1 | 12/2005 | Heller et al. |
| 2006/0001538 A1 | 1/2006 | Kraft et al. |
| 2006/0001550 A1 | 1/2006 | Mann et al. |
| 2006/0001551 A1 | 1/2006 | Kraft et al. |
| 2006/0003398 A1 | 1/2006 | Heller et al. |
| 2006/0004271 A1 | 1/2006 | Peyser et al. |
| 2006/0007017 A1 | 1/2006 | Mann et al. |
| 2006/0015020 A1 | 1/2006 | Neale et al. |
| 2006/0015024 A1 | 1/2006 | Brister et al. |
| 2006/0016700 A1 | 1/2006 | Brister et al. |
| 2006/0019327 A1 | 1/2006 | Brister et al. |
| 2006/0020186 A1 | 1/2006 | Brister et al. |
| 2006/0020187 A1 | 1/2006 | Brister et al. |
| 2006/0020188 A1 | 1/2006 | Kamath et al. |
| 2006/0020189 A1 | 1/2006 | Brister et al. |
| 2006/0020190 A1 | 1/2006 | Kamath et al. |
| 2006/0020191 A1 | 1/2006 | Brister et al. |
| 2006/0020192 A1 | 1/2006 | Brister et al. |
| 2006/0025663 A1 | 2/2006 | Talbot et al. |
| 2006/0031094 A1 | 2/2006 | Cohen et al. |
| 2006/0036139 A1 | 2/2006 | Brister et al. |
| 2006/0036140 A1 | 2/2006 | Brister et al. |
| 2006/0036141 A1 | 2/2006 | Kamath et al. |
| 2006/0036142 A1 | 2/2006 | Brister et al. |
| 2006/0036143 A1 | 2/2006 | Brister et al. |
| 2006/0036144 A1 | 2/2006 | Brister et al. |
| 2006/0036145 A1 | 2/2006 | Brister et al. |
| 2006/0036187 A1 | 2/2006 | Vos et al. |
| 2006/0040402 A1 | 2/2006 | Brauker et al. |
| 2006/0052679 A1 | 3/2006 | Kotulla et al. |
| 2006/0058602 A1 | 3/2006 | Kwiatkowski et al. |
| 2006/0058627 A1 | 3/2006 | Flaherty et al. |
| 2006/0063218 A1 | 3/2006 | Bartkowiak et al. |
| 2006/0074564 A1 | 4/2006 | Bartkowiak et al. |
| 2006/0166629 A1 | 7/2006 | Reggiardo |
| 2006/0173259 A1 | 8/2006 | Flaherty et al. |
| 2006/0173444 A1 | 8/2006 | Choy et al. |
| 2006/0222566 A1 | 10/2006 | Brauker et al. |
| 2006/0224141 A1 | 10/2006 | Rush et al. |
| 2006/0247508 A1 | 11/2006 | Fennell |
| 2006/0273759 A1 | 12/2006 | Reggiardo |
| 2007/0016381 A1 | 1/2007 | Kamath et al. |
| 2007/0078323 A1 | 4/2007 | Reggiardo et al. |
| 2007/0106135 A1 | 5/2007 | Sloan |
| 2007/0135697 A1 | 6/2007 | Reggiardo |
| 2007/0163880 A1 | 7/2007 | Woo et al. |
| 2007/0173711 A1 | 7/2007 | Shah et al. |
| 2007/0176867 A1 | 8/2007 | Reggiardo et al. |
| 2007/0203966 A1 | 8/2007 | Brauker et al. |
| 2007/0235331 A1 | 10/2007 | Simpson et al. |
| 2008/0021666 A1 | 1/2008 | Goode, Jr. et al. |
| 2008/0033254 A1 | 2/2008 | Kamath et al. |
| 2008/0045824 A1 | 2/2008 | Tapsak et al. |
| 2008/0064941 A1 | 3/2008 | Funderburk et al. |
| 2008/0071156 A1 | 3/2008 | Brister et al. |
| 2008/0083617 A1 | 4/2008 | Simpson et al. |
| 2008/0086042 A1 | 4/2008 | Brister et al. |
| 2008/0086044 A1 | 4/2008 | Brister et al. |
| 2008/0086273 A1 | 4/2008 | Shults et al. |
| 2008/0108942 A1 | 5/2008 | Brister et al. |
| 2008/0183061 A1 | 7/2008 | Goode et al. |
| 2008/0183399 A1 | 7/2008 | Goode et al. |
| 2008/0188731 A1 | 8/2008 | Brister et al. |
| 2008/0189051 A1 | 8/2008 | Goode et al. |
| 2008/0194935 A1 | 8/2008 | Brister et al. |
| 2008/0194936 A1 | 8/2008 | Goode et al. |
| 2008/0194937 A1 | 8/2008 | Goode et al. |
| 2008/0194938 A1 | 8/2008 | Brister et al. |
| 2008/0195232 A1 | 8/2008 | Carr-Brendel et al. |
| 2008/0195967 A1 | 8/2008 | Goode et al. |
| 2008/0197024 A1 | 8/2008 | Simpson et al. |
| 2008/0200788 A1 | 8/2008 | Brister et al. |
| 2008/0200789 A1 | 8/2008 | Brister et al. |
| 2008/0200791 A1 | 8/2008 | Simpson et al. |
| 2008/0208025 A1 | 8/2008 | Shults et al. |
| 2008/0214915 A1 | 9/2008 | Brister et al. |
| 2008/0214918 A1 | 9/2008 | Brister et al. |
| 2008/0228051 A1 | 9/2008 | Shults et al. |
| 2008/0228054 A1 | 9/2008 | Shults et al. |
| 2008/0242961 A1 | 10/2008 | Brister et al. |
| 2008/0262469 A1 | 10/2008 | Brister et al. |
| 2008/0275313 A1 | 11/2008 | Brister et al. |
| 2008/0287764 A1 | 11/2008 | Rasdal et al. |
| 2008/0287765 A1 | 11/2008 | Rasdal et al. |
| 2008/0287766 A1 | 11/2008 | Rasdal et al. |
| 2008/0296155 A1 | 12/2008 | Shults et al. |
| 2008/0306368 A1 | 12/2008 | Goode et al. |
| 2008/0306434 A1 | 12/2008 | Dobbles et al. |
| 2008/0306435 A1 | 12/2008 | Kamath et al. |
| 2008/0306444 A1 | 12/2008 | Brister et al. |
| 2009/0012379 A1 | 1/2009 | Goode et al. |
| 2009/0018424 A1 | 1/2009 | Kamath et al. |
| 2009/0030294 A1 | 1/2009 | Petisce et al. |
| 2009/0036758 A1 | 2/2009 | Brauker et al. |

| | | |
|---|---|---|
| 2009/0036763 A1 | 2/2009 | Brauker et al. |
| 2009/0043181 A1 | 2/2009 | Brauker et al. |
| 2009/0043182 A1 | 2/2009 | Brauker et al. |
| 2009/0043525 A1 | 2/2009 | Brauker et al. |
| 2009/0043541 A1 | 2/2009 | Brauker et al. |
| 2009/0043542 A1 | 2/2009 | Brauker et al. |
| 2009/0045055 A1 | 2/2009 | Rhodes et al. |
| 2009/0062633 A1 | 3/2009 | Brauker et al. |
| 2009/0062635 A1 | 3/2009 | Brauker et al. |
| 2009/0076356 A1 | 3/2009 | Simpson et al. |
| 2009/0076360 A1 | 3/2009 | Brister et al. |
| 2009/0076361 A1 | 3/2009 | Kamath et al. |
| 2009/0099436 A1 | 4/2009 | Brister et al. |
| 2009/0124877 A1 | 5/2009 | Goode, Jr. et al. |
| 2009/0124878 A1 | 5/2009 | Goode et al. |
| 2009/0124879 A1 | 5/2009 | Brister et al. |
| 2009/0124964 A1 | 5/2009 | Leach et al. |
| 2009/0131768 A1 | 5/2009 | Simpson et al. |
| 2009/0131769 A1 | 5/2009 | Leach et al. |
| 2009/0131776 A1 | 5/2009 | Simpson et al. |
| 2009/0131777 A1 | 5/2009 | Simpson et al. |
| 2009/0137886 A1 | 5/2009 | Shariati et al. |
| 2009/0137887 A1 | 5/2009 | Shariati et al. |
| 2009/0143659 A1 | 6/2009 | Ying et al. |
| 2009/0143660 A1 | 6/2009 | Brister et al. |
| 2009/0156919 A1 | 6/2009 | Brister et al. |
| 2009/0156924 A1 | 6/2009 | Shariati et al. |
| 2009/0163790 A1 | 6/2009 | Brister et al. |
| 2009/0163791 A1 | 6/2009 | Brister et al. |
| 2009/0178459 A1 | 7/2009 | Li et al. |
| 2009/0182217 A1 | 7/2009 | Li et al. |
| 2009/0192366 A1 | 7/2009 | Mensinger et al. |
| 2009/0192380 A1 | 7/2009 | Shariati et al. |
| 2009/0192722 A1 | 7/2009 | Shariati et al. |
| 2009/0192724 A1 | 7/2009 | Brauker et al. |
| 2009/0192745 A1 | 7/2009 | Kamath et al. |
| 2009/0192751 A1 | 7/2009 | Kamath et al. |
| 2009/0203981 A1 | 8/2009 | Brauker et al. |
| 2009/0204341 A1 | 8/2009 | Brauker et al. |
| 2009/0216103 A1 | 8/2009 | Brister et al. |
| 2009/0240120 A1 | 9/2009 | Mensinger et al. |
| 2009/0240128 A1 | 9/2009 | Mensinger et al. |
| 2009/0240193 A1 | 9/2009 | Mensinger et al. |
| 2009/0242399 A1 | 10/2009 | Kamath et al. |
| 2009/0242425 A1 | 10/2009 | Kamath et al. |
| 2009/0247855 A1 | 10/2009 | Boock et al. |
| 2009/0247856 A1 | 10/2009 | Boock et al. |
| 2009/0287073 A1 | 11/2009 | Boock et al. |
| 2009/0287074 A1 | 11/2009 | Shults et al. |
| 2009/0299155 A1 | 12/2009 | Yang et al. |
| 2009/0299156 A1 | 12/2009 | Simpson et al. |
| 2009/0299162 A1 | 12/2009 | Brauker et al. |
| 2009/0299276 A1 | 12/2009 | Brauker et al. |

FOREIGN PATENT DOCUMENTS

| | | |
|---|---|---|
| EP | 0878707 | 11/1998 |
| EP | 0543916 | 7/2001 |
| EP | 1130638 | 9/2001 |
| EP | 1755443 | 11/2005 |
| JP | 2001-177423 | 6/2001 |
| JP | 2001-056673 | 11/2001 |
| WO | WO 99/22236 | 5/1999 |
| WO | WO 01/52727 | 7/2001 |
| WO | WO-2002/084860 | 10/2002 |
| WO | WO-2004/028337 | 4/2004 |
| WO | WO-2004/032994 | 4/2004 |
| WO | WO-2004/061420 | 7/2004 |
| WO | WO-2005/089103 | 9/2005 |
| WO | WO-2005/101994 | 11/2005 |
| WO | WO 2006/079114 | 7/2006 |
| WO | WO-2006/102412 | 9/2006 |
| WO | WO-2006/110913 | 10/2006 |
| WO | WO-2006/113408 | 10/2006 |
| WO | WO-2006/113521 | 10/2006 |
| WO | WO-2006/118947 | 11/2006 |
| WO | WO-2006/132884 | 12/2006 |
| WO | WO-2007/041072 | 4/2007 |
| WO | WO-2007/090037 | 8/2007 |
| WO | WO 2008/055037 | 5/2008 |

OTHER PUBLICATIONS

"An Electrochemical Slow Flow Meter", http://gore.ocean.washington.edu/research/slow_flow_meter.html, 2005, 3 pages.

Bard, A. J., et al., "Methods Involving Forced Convection—Hydrodynamic Methods", *Electrochemical Methods—Fundamentals and Applications*, 2001, pp. 331-367.

Kissinger, P. T., "Introduction to Analog Instrumentation", *Laboratory Techniques in Electroanalytical Chemistry, Second Edition, Revised and Expanded*, 1996, pp. 165-194.

Ursino, M, et al., "A Mathematical Model of Cerebral Blood Flow Chemical Regulation—Part I: Diffusion Processes", *IEEE Transactions on Biomedical Engineering*, vol. 36, No. 2, 1989, pp. 183-191.

* cited by examiner

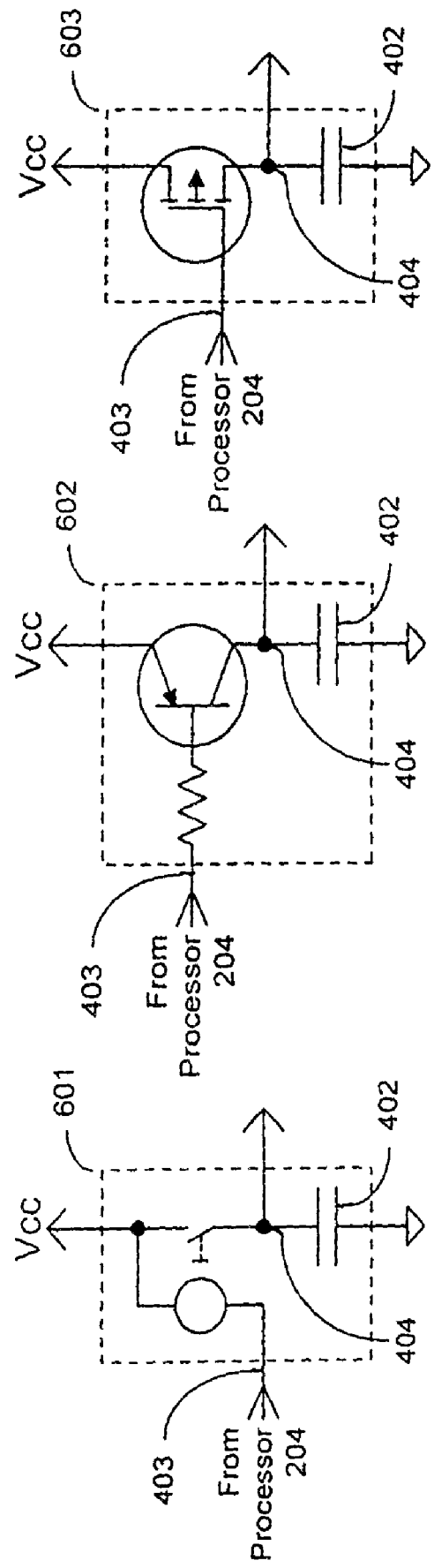

METHOD AND APPARATUS FOR PROVIDING PEAK DETECTION CIRCUITRY FOR DATA COMMUNICATION SYSTEMS

RELATED APPLICATION

This application claims priority under 35 USC §119(e) to Application No. 60/466,243 filed Apr. 28, 2003 entitled "Method and Apparatus for Providing Peak Detection Circuitry for Data Communication Systems" and assigned to TheraSense, Inc., assignee of the present application, and the disclosure of which is incorporated herein by reference for all purposes.

BACKGROUND

The present invention relates to communication systems. More specifically, the present invention relates to radio frequency (RF) communication systems for data communication between portable electronic devices such as in continuous glucose monitoring systems.

Continuous glucose monitoring systems generally include a small, lightweight battery powered and microprocessor controlled system which is configured to detect signals proportional to the corresponding measured glucose levels using an electrometer, and RF signals to transmit the collected data. When the microprocessor is active or when the system is in the process of processing or transmitting data, the battery power supply may display a loading effect commonly referred to as "drooping" due to the current consumption of the microprocessor operation or the transmit function compared to the average current draw level.

The voltage drooping may occur when the processor (or controller) for the transmitter initiates and performs a configured procedure, or alternatively, in the case where the RF transmitter initiates data transmission. For example, the processor may draw a small amount of current in idle state (for example, 1 µA), while in active processing mode, it may draw as much as 2 mA. Additionally, the RF transmitter may draw approximately 10 mA during data transmission state.

The drooping effect is particularly prominent after a portion of the available battery energy has been consumed (that is, the battery energy is partially discharged) and is typical for small batteries where size, weight and power density are optimized versus peak current capacity. This, in turn, may have a negative impact on the processing of detected signals such as by signal degradation or data loss, and importantly, may adversely affect the delicate electrometer and the analog circuitry in the transmitter unit of the monitoring system. More specifically, when the analog front end circuitry in the transmitter of the monitoring system is disturbed, there may be a several second delay when the data may be unusable and a longer delay (for example, on the order of 10 seconds) when the data may be unreliable or beyond the tolerance range of desired accuracy.

In view of the foregoing, it would be desirable to isolate the delicate electrometer and the analog circuitry of the monitoring system, for example, in the transmitting side, from the adverse effects of battery voltage drooping using simple, low cost and low noise approaches, in contrast to the existing techniques using, for example, a DC to DC converter which typically has higher cost as well as higher noise.

SUMMARY OF THE INVENTION

Accordingly, in one embodiment of the present invention, there is provided a peak detection circuit comprising a diode including an input terminal and an output terminal the input terminal of the diode configured to receive an input signal, a capacitor operatively coupled to the output terminal of the diode, and an output terminal operatively coupled to the capacitor and the output terminal of the diode for outputting an output signal.

The diode may include a Schottky diode switch, and further, the input signal may include a voltage signal from a power supply.

Moreover, in one embodiment, a voltage droop may be detected at the input terminal of the diode, and where the diode and the capacitor may be configured to compensate for the voltage droop.

In a further embodiment of the present invention, there is provided a data communication system including peak detection circuit comprising a peak detection circuit configured to receive a power supply signal, and further to output a detected signal, and a low pass filter operatively coupled to the detection circuit, the detection circuit configured to receive the detected signal, where the peak detection circuit may be configured to detect a voltage droop in the power supply signal and further, to compensate for the voltage droop.

In a further embodiment, the peak detection circuit may be configured to electrically isolate the detected voltage droop.

Additionally, the peak detection circuit may in an alternate embodiment include a passive switching configuration.

Also, the peak detection circuit may in one embodiment include a diode operatively coupled to a capacitance, where the diode may include a Schottky diode switch.

In accordance with yet another embodiment of the present invention, there is provide a method of providing a peak detection circuit, comprising the steps of providing a diode having an input terminal and an output terminal the input terminal of the diode configured to receive an input signal, operatively coupling a capacitor to the output terminal of the diode, and operatively coupling an output terminal to the capacitor and the output terminal of the diode for outputting an output signal.

Also, the input signal may include a voltage signal from a power supply.

Moreover, in a further embodiment, the method may further include the steps of detecting a voltage droop at the input terminal of the diode, and compensating for the voltage droop by the diode and the capacitor.

In accordance with still another embodiment of the present invention, there is provided a method of providing peak detection in a data communication system, comprising the steps of configuring a peak detection circuit to detect a voltage droop in a power supply signal and to output a compensated signal, low pass filtering the compensated signal from the peak detection circuit.

In one embodiment, the step of configuring the peak detection circuit may further include the step of electrically isolating the detected voltage droop.

Moreover, the step of providing the peak detection circuit may include providing a passive switching configuration.

Additionally, the step of configuring the peak detection circuit may include the step of operatively coupling a diode to a capacitance.

Indeed, in accordance with the various embodiments of the present invention, there is provided a peak detection circuit in the transmitter of a data communication system which is configured to detect a voltage droop from its power supply such as a battery configured to power the transmitter, and to effectively compensate for the detected voltage signal droop such that the delicate circuitry of the electrometer and the analog front end circuitry of the transmitter unit may be electrically isolated (for example, by switching off the connection between the electrometer and the analog front end circuitry, and the power supply source) from the detected voltage drooping while the necessary current is drawn from another source such as a capacitor to support the required voltage level of the electrometer and the analog front end circuitry.

The peak detection circuit in one aspect may include passive switching configurations with a diode and a capacitor combination. In addition, a low pass filter may be operatively coupled to the peak detection circuit to filter out any switching noise transients. In an alternate embodiment, the peak detection circuit may include active components such as a relay switch, a BJT or FET transistor switch. In this case, the switching mechanism is controlled by the processor to turn the switch on or off, in case of power supply voltage drooping, as opposed to the passive component configuration with the diode, in which case such voltage drooping is automatically detected and the switching mechanism of the peak detection circuit accordingly operated in response thereto.

Furthermore, as discussed above, the diode used for the peak detection circuit may include a Schottky diode switch. Moreover, the peak detection circuit in one embodiment may be provided between the power supply and the analog front end circuitry of the transmitter unit in the continuous glucose monitoring system such that in the case where power supply voltage drooping occurs, the peak detection circuit may be configured to isolate the delicate circuitry of the analog front end of the transmitter unit from the power supply, and rather allow the electrometer and the analog front end circuitry of the transmitter to draw the necessary power from a capacitor of the peak detection circuit to ensure continuous and proper operation.

Accordingly, in accordance with the various embodiments of the present invention, by using a peak detection circuit with a tuned low pass filter, an effective, low cost and low noise approach to isolating the battery droop, even that in excess of 0.5 volts, may be achieved such that in the monitoring system discussed above, the detected and processed data values are not substantially effected, and the delicate analog circuitry of the transmitter is not adversely effected by the fluctuation in power supply signal.

INCORPORATION BY REFERENCE

Applicants herein incorporate by reference application Ser. No. 09/753,746 filed on Jan. 2, 2001 entitled "Analyte Monitoring Device and Methods of Use", and Application No. 60/437,374 filed Dec. 31, 2002 entitled "Continuous Glucose Monitoring System and Methods of Use" each assigned to the Assignee of the present application for all purposes.

BRIEF DESCRIPTION OF THE DRAWINGS

FIGS. 6A-6C illustrate the peak detection circuits implemented using active components in accordance with several alternate embodiments of the present invention.

DETAILED DESCRIPTION

Figure 1:
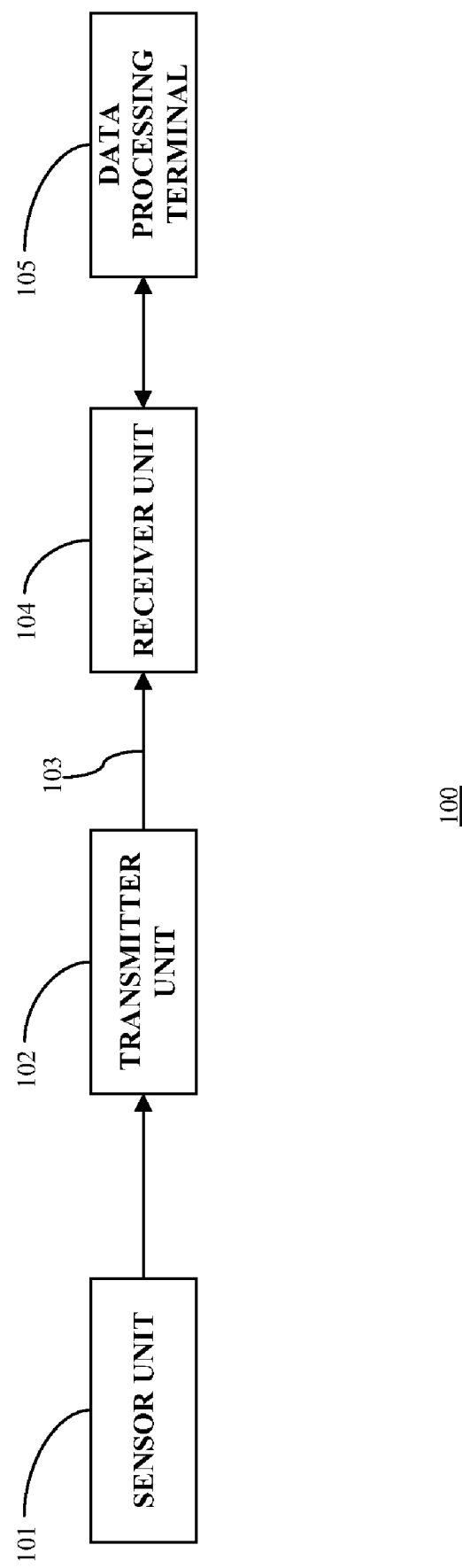
FIG. 1 illustrates a block diagram of an overall communication system for practicing one embodiment of the present invention.

FIG. 1 illustrates a data communication system such as, for example, a continuous glucose monitoring system 100 in accordance with one embodiment of the present invention. In such an embodiment, the continuous glucose monitoring system 100 includes a sensor 101, a transmitter 102 coupled to the sensor 101, and a receiver 104 which is configured to communicate with the transmitter 102 via a communication link 103. The receiver 104 may be further configured to transmit data to a data processing terminal 105 for evaluating the data received by the receiver 104. Only one sensor 101, transmitter 102, communication link 103, receiver 104, and data processing terminal 105 are shown in the embodiment of the continuous glucose monitoring system 100 illustrated in FIG. 1. However, it will be appreciated by one of ordinary skill in the art that the continuous glucose monitoring system 100 may include one or more sensor 101, transmitter 102, communication link 103, receiver 104, and data processing terminal 105, where each receiver 104 is uniquely synchronized with a respective transmitter 102.

In one embodiment of the present invention, the sensor 101 is physically positioned on the body of a user whose glucose level is being monitored. The sensor 101 is configured to continuously sample the glucose level of the user and convert the sampled glucose level into a corresponding data signal for transmission by the transmitter 102. In one embodiment, the transmitter 102 is mounted on the sensor 101 so that both devices are positioned on the user's body. The transmitter 102 performs data processing such as filtering and encoding on data signals, each of which corresponds to a sampled glucose level of the user, for transmission to the receiver 104 via the communication link 103.

In one embodiment, the continuous glucose monitoring system 100 is configured as a one-way RF communication path from the transmitter 102 to the receiver 104. In such embodiment, the transmitter 102 transmits the sampled data signals received from the sensor 101 without acknowledgement from the receiver 104 that the transmitted sampled data signals have been received. For example, the transmitter 102 may be configured to transmit the encoded sampled data signals at a fixed rate (e.g., at one minute intervals) after the completion of the initial power on procedure. Likewise, the receiver 104 may be configured to detect such transmitted encoded sampled data signals at predetermined time intervals. Alternatively, in accordance with a further embodiment of the present invention, the continuous glucose monitoring system 100 may be configured with a two-way RF communication path between the transmitter 102 and the receiver 104 using transceivers.

Additionally, in one aspect, the receiver 104 may include two sections. The first section is an analog interface section that is configured to communicate with the transmitter 102 via the communication link 103. In one embodiment, the analog interface section may include an RF receiver and an antenna for receiving and amplifying the data signals from the transmitter 102, which are thereafter, demodulated with a local oscillator and filtered through a band-pass filter. The second section of the receiver 104 is a data processing section which is configured to process the data signals received from the transmitter 102 such as by performing data decoding, error detection and correction, data clock generation, and data bit recovery.

In operation, upon completing the power-on procedure, the receiver 104 is configured to detect the presence of the transmitter 102 within its range based on, for example, the strength of the detected data signals received from the transmitter 102 or a predetermined transmitter identification information. Upon successful synchronization with the corresponding transmitter 102, the receiver 104 is configured to begin receiving from the transmitter 102 data signals corresponding to the user's detected glucose level. More specifically, the receiver 104 in one embodiment is configured to perform synchronized time hopping with the corresponding synchronized transmitter 102 via the communication link 103 to obtain the user's detected glucose level.

Referring again to FIG. 1, the data processing terminal 105 may include a personal computer, a portable computer such as a laptop or a handheld device (e.g., personal digital assistants (PDAs)), and the like, each of which may be configured for data communication with the receiver via a wired or a wireless connection. Additionally, the data processing terminal 105 may further be connected to a data network (not shown) for storing, retrieving and updating data corresponding to the detected glucose level of the user.

Figure 2:
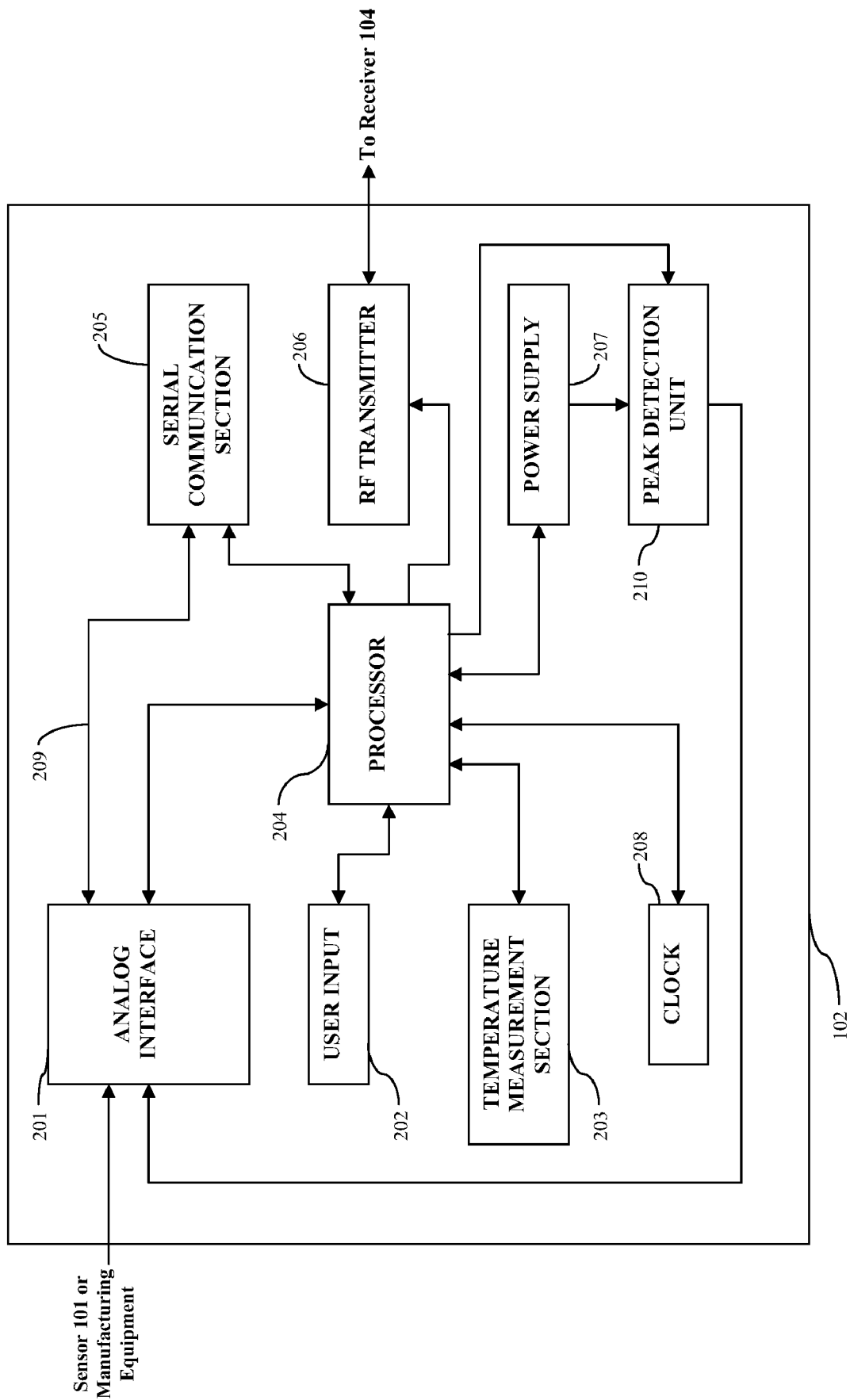
FIG. 2 is a block diagram of the transmitter of the overall communication system shown in FIG. 1 in accordance with one embodiment of the present invention.

FIG. 2 is a block diagram of the transmitter of the overall communication system shown in FIG. 1 in accordance with one embodiment of the present invention. Referring to the Figure, the transmitter 102 in one embodiment includes an analog interface 201 configured to communicate with the sensor 101 (FIG. 1), a user input 202, and a temperature detection section 203, each of which is operatively coupled to a transmitter processor 204 such as a central processing unit (CPU). Further shown in FIG. 2 are a transmitter serial communication section 205 and an RF transmitter 206, each of which is also operatively coupled to the transmitter processor 204. Moreover, a power supply 207 such as a battery is also provided in the transmitter 102 to provide the necessary power for the transmitter 102. Additionally, as can be seen from the Figure, clock 208 is provided to, among others, supply real time information to the transmitter processor 204. Also shown in FIG. 2 is a peak detection unit 210 operatively coupled to the analog interface 201, the processor 204 and the power supply 207.

In one embodiment, a unidirectional input path is established from the sensor 101 (FIG. 1) and/or manufacturing and testing equipment to the analog interface 201 of the transmitter 102, while a unidirectional output is established from the output of the RF transmitter 206 of the transmitter 102 for transmission to the receiver 104. In this manner, a data path is shown in FIG. 2 between the aforementioned unidirectional input and output via a dedicated link 209 from the analog interface 201 to serial communication section 205, thereafter to the processor 204, and then to the RF transmitter 206. As such, in one embodiment, via the data path described above, the transmitter 102 is configured to transmit to the receiver 104 (FIG. 1), via the communication link 103 (FIG. 1), processed and encoded data signals received from the sensor 101 (FIG. 1). Additionally, the unidirectional communication data path between the analog interface 201 and the RF transmitter 206 discussed above allows for the configuration of the transmitter 102 for operation upon completion of the manufacturing process as well as for direct communication for diagnostic and testing purposes.

As discussed above, the transmitter processor 204 is configured to transmit control signals to the various sections of the transmitter 102 during the operation of the transmitter 102. In one embodiment, the transmitter processor 204 also includes a memory (not shown) for storing data such as the identification information for the transmitter 102, as well as the data signals received from the sensor 101. The stored information may be retrieved and processed for transmission to the receiver 104 under the control of the transmitter processor 204. Furthermore, the power supply 207 may include a commercially available battery.

The transmitter 102 is also configured such that the power supply section 207 is capable of providing power to the transmitter for a minimum of three months of continuous operation after having been stored for 18 months in a low-power (non-operating) mode. In one embodiment, this may be achieved by the transmitter processor 204 operating in low power modes in the non-operating state, for example, drawing no more than approximately 1 µA of current. Indeed, in one embodiment, the final step during the manufacturing process of the transmitter 102 may place the transmitter 102 in the lower power, non-operating state (i.e., post-manufacture sleep mode). In this manner, the shelf life of the transmitter 102 may be significantly improved.

Referring yet again to FIG. 2, the temperature detection section 203 of the transmitter 102 is configured to monitor the temperature of the skin near the sensor insertion site. The temperature reading is used to adjust the glucose readings obtained from the analog interface 201. The RF transmitter 206 of the transmitter 102 may be configured for operation in the frequency band of 315 MHz to 322 MHz, for example, in the United States. Further, in one embodiment, the RF transmitter 206 is configured to modulate the carrier frequency by performing Frequency Shift Keying and Manchester encoding. In one embodiment, the data transmission rate is 19,200 symbols per second, with a minimum transmission range for communication with the receiver 104.

Additional detailed description of the continuous glucose monitoring system, its various components including the functional descriptions of the transmitter are provided in application Ser. No. 09/753,746 filed on Jan. 2, 2001 entitled "Analyte Monitoring Device and Methods of Use", and in application No. 60/437,374 filed Dec. 31, 2002 entitled "Continuous Glucose Monitoring System and Methods of Use", each assigned to the Assignee of the present application, and the disclosures of each of which are incorporated herein by reference for all purposes.

Figure 3:
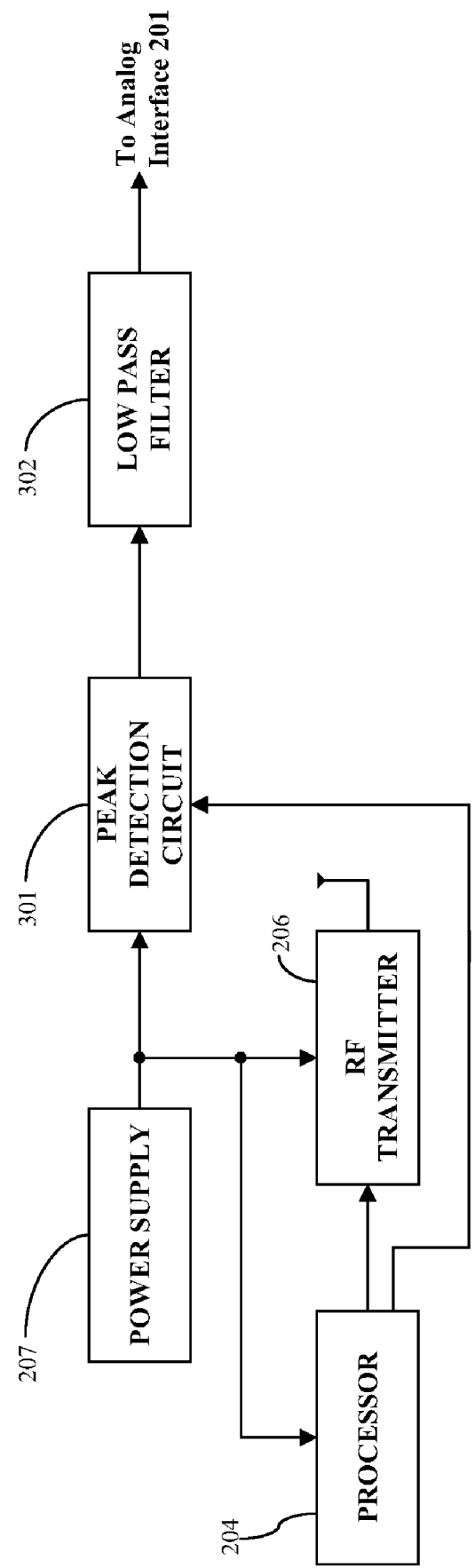
FIG. 3 is a block diagram illustrating the peak detection system in the transmitter of FIG. 2 in accordance with embodiment of the present invention.

FIG. 3 is a block diagram illustrating the peak detection unit 210 in the transmitter of FIG. 2 in accordance with embodiment of the present invention. Referring to the Figure, there is shown a peak detection circuit 301 operatively coupled between the power supply 207 and a low pass filter 302. As further shown in FIG. 3, the power supply 207 is further operatively coupled to the processor 204 and the RF transmitter 206. The low pass filter 302 is additionally operatively coupled to the analog interface 201 (FIG. 2) which includes delicate circuitry for detecting and processing signals corresponding to the glucose level detected by the sensor unit 101 (FIG. 1), and powered by the power supply 207.

The processor 204 may draw a small amount of current in idle state (for example, 1 µA) as described above, while in active processing mode, the processor 204 may draw as much as 2 mA of current. Additionally, the RF transmitter 206 may draw approximately 10 mA of current during data transmission state. Either case of the processor 204 in active processing mode or the RF transmitter 206 in data transmission mode may result in voltage drooping from the power supply 207.

Accordingly, the peak detection circuit 301 in accordance with one embodiment is configured to detect the occurrences of the power supply voltage drooping, and to switch off the connection of the power supply 207 to the analog interface 201. In this case, the analog interface 201 may be configured to draw the necessary current from, for example, a capacitor of the peak detection circuit 301 to support the voltage necessary for operation. This will be discussed in further detail below in conjunction with the embodiments illustrated in FIGS. 4 and 5A-5C. Additionally, the low pass filter 302 in one embodiment may be configured to filter out any resulting switching noise transients also discussed in further detail below.

Figure 4:
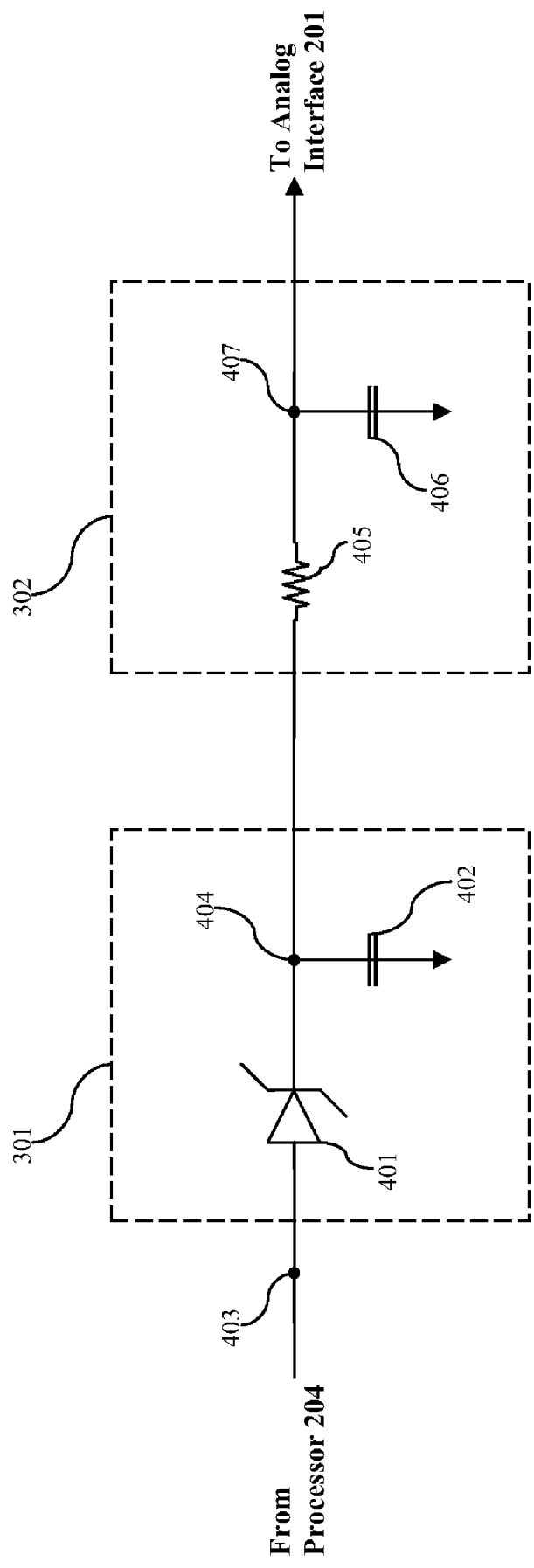
FIG. 4 illustrates the peak detection circuit and the low pass filter of the peak detection system shown in FIG. 3 in accordance with one embodiment of the present invention.

FIG. 4 illustrates the peak detection circuit and the low pass filter of the peak detection unit shown in FIG. 3 in accordance with one embodiment of the present invention. Referring to the Figure, the peak detection circuit 301 in one embodiment includes a diode 401 operatively coupled to a capacitor 402. The diode in one embodiment may be a Schottky diode configured to operate as a switch, while the capacitor 402 may, in one embodiment have a value of approximately 10 μFarads.

Referring back to FIG. 4, the low pass filter 302 in one embodiment may include a resistor 405 operatively coupled between the peak detection circuit 301 and the interface to the analog front end circuitry, and a capacitor 406 further operatively coupled to the resistor 405. In one embodiment, the resistor 405 may have a value of 1 kOhms, while the capacitor 406 may have a value of approximately 1 μFarads. In this manner, the configuration of the resistor 405 and the capacitor 406 effectively establishes a low pass RC filter.

Referring again to FIG. 4, while any suitable diode may be used for diode 401 in the peak detection circuit 301, the Schottky diode as shown in the Figure may be used to take advantage of its properties including a lower forward voltage drop as compared to conventional diodes. This, in turn, allows the capacitor 402 of the peak detection circuit 301 to charge to a higher value, as there is a smaller voltage drop from the voltage at the input terminal 403 and the output terminal 404 of the peak detection circuit 301 under steady state conditions. In accordance with one embodiment of the present invention, the low pass RC filter 302 shown in the Figure may be implemented for each chip connected to the power supply of the analog front end circuitry.

Furthermore, in one embodiment, the diode 401 of the peak detection circuit 301 may be directly coupled to the battery or to a switched power supply source (for example, power supply 207 (FIGS. 2 and 3)). Also, the output of the processor 204 in one aspect may be used to drive the diode 401 of the peak detection circuit 301 such that the analog front end circuitry may be switched off to increase the storage (for example, post manufacture sleep mode) period when the system is being transported to the users. This approach is possible when the processor 204 output drive signal level is sufficient to power the analog front end circuitry with no noticeable output voltage droop due to loading.

Additionally, it should be noted that the low pass filter 302 in one embodiment may be configured to prevent the high frequency switching noise of the processor 204 from adversely affecting the analog front end circuitry. More specifically, since the processor 204 displays high frequency switching noise on the order of 1 MHz, a low pass filter with a cut-off frequency of, for example, 1 kHz would reduce the switching nose to approximately 0.1% or less. For example, with a 1 kOhm resistor 405 and a 1 μFarad capacitor 406 forming the low pass filter 302, the cut-off frequency is established at 1 kHz such that any signal of higher frequency than the cut-off frequency will be attenuated. In one embodiment, the low pass filter values (i.e., the values of the resistor 405 and the capacitor 406) may be varied or optimized for a given processor 204 and circuit implementation.

In the manner described above, in accordance with one embodiment of the present invention, the peak detection circuit 301 and the low pass filter 302 may be configured to provide an effective safeguard against any potential perturbation in the outputs of any circuitry operatively coupled to the analog front end circuitry (e.g., at terminal 407 shown in FIG. 4) resulting from voltage drooping of the power supply 207. In the case of the continuous glucose monitoring system discussed above, this translates to less than one least significant bit (lsb) of data change on the electrometer output as measured by an analog to digital converter during processor 204 activity or during a data transmit occurrence. In a further embodiment, the low pass filter values (i.e., the values of the resistor 405 and the capacitor 406) may be further varied or optimized for a given Power Supply Rejection Ratio (PSRR) of the analog circuitry.

Figure 5A:
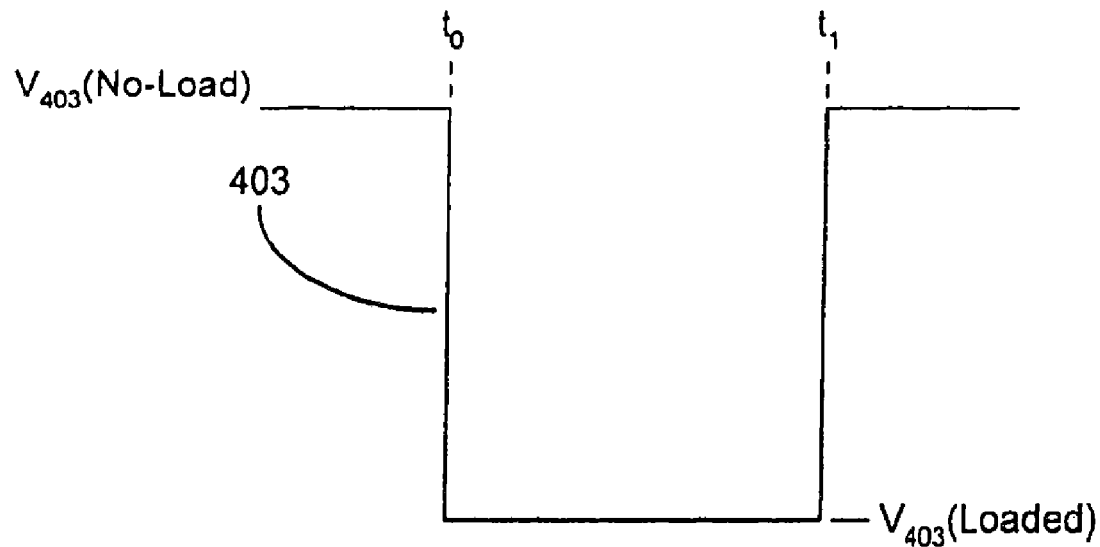
FIGS. 5A-5C illustrate the signal levels at the input to the peak detection circuit, between the output of the peak detection circuit and the input to the low pass filter, and at the output of the low pass filter, respectively, in accordance with one embodiment of the present invention.
Figure 5B:
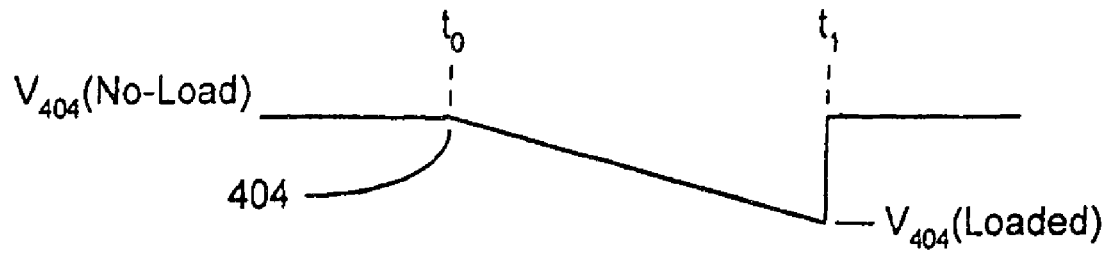
Figure 5C:
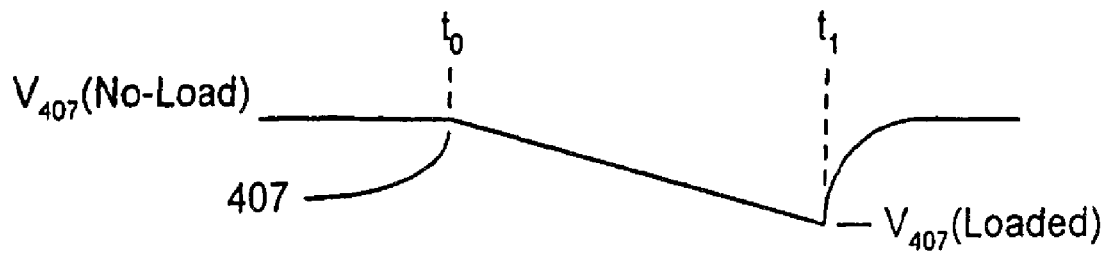

FIGS. 5A-5C illustrate the signal levels at the input to the peak detection circuit, between the output of the peak detection circuit and the input to the low pass filter, and at the output of the low pass filter, respectively, in accordance with one embodiment of the present invention. Referring to FIGS. 5 and 5A-5C, the signal waveform at the input terminal 403 to the peak detection circuit 301 (FIG. 4) is shown in FIG. 5A over the time period $t_0$ to $t_1$, while the signal waveform at the output terminal 404 of the peak detection circuit 301 is shown in FIG. 5B, and the low pass filtered signal at the output terminal 407 of the low pass filter 302 (FIG. 4) is shown in FIG. 5C.

FIGS. 6A-6C illustrate the peak detection circuits implemented using active components in accordance with alternate embodiments of the present invention. More specifically, FIGS. 6A-6C respectively illustrate a relay circuitry 601, a pnp bipolar junction transistor (BJT) switch 602, and a PMOS field effect transistor (FET) switch 603, each configured to operate as active peak detection circuits in accordance with alternate embodiments of the present invention. In the embodiments shown in FIGS. 6A-6C, the peak detection circuits 601-603 are implemented as an inverter so that a low input signal closes the switch, and charges the capacitor, driving the load circuit (e.g., the analog front end circuitry), and a high input signal causes the switch to open and the load circuit in such case is powered by the energy stored in the capacitor.

As each of the switches shown in FIGS. 6A-6C are active switches, they each must be actively switched on and off by the processor 204 each time a voltage drooping is anticipated. By contrast, the passive peak detection circuit using the diode switching system does not require active switching by the processor 204, but rather, is configured to automatically detect such voltage drop due to processor 204 activity or based on the detection of data transmit activities.

By way of example, in the case of using the relay switch 601 or the FET switch 603 as the peak detection circuit 301, the voltage drop between the power supply 207 voltage coupled to the input terminal 403 of the peak detection circuit 301, and the voltage supplied to the analog front end circuitry (for example, at terminal 407 in FIG. 4). may be in the order of 5 mVolts, while the embodiment discussed above using the diode 401 (FIG. 4) may have a 100 mV drop.

In the manner described above, in accordance with the various embodiments of the present invention, there is provided a method and apparatus for isolating potential voltage droop from the power supply 204 to the delicate circuitry of the analog front end in a simple, and cost effective manner while maintaining the level of noise to a minimum.

More specifically, there is provided in one embodiment, a peak detection circuit in the transmitter unit of a data communication system which is configured to detect a voltage droop from its power supply such as a battery configured to power the transmitter, and to effectively compensate for the detected voltage signal droop such that the delicate circuitry of the electrometer and the analog front end circuitry of the transmitter unit may be electrically isolated (for example, by switching off the connection between the electrometer and the analog front end circuitry, and the power supply source) from the detected voltage drooping while the necessary current is drawn from another source such as a capacitor to support the required voltage level of the electrometer and the analog front end circuitry.

The peak detection circuit may include passive switching configurations with a diode and a capacitor combination. In addition, a low pass filter may be operatively coupled to the peak detection circuit to filter out any switching noise transients. In an alternate embodiment, the peak detection circuit may include active components such as a relay switch, a BJT or FET transistor switch. In this case, the switching mechanism is controlled by the processor to turn the switch on or off, in case of power supply voltage drooping, as opposed to the passive component configuration with the diode, in which case such voltage drooping is automatically detected and the switching mechanism of the peak detection circuit accordingly operated in response thereto.

In one embodiment, the diode used for the peak detection circuit may include a Schottky diode switch. Moreover, the peak detection circuit in one embodiment may be provided between the power supply and the analog front end circuitry of the transmitter unit in the continuous glucose monitoring system such that in cases where power supply voltage drooping occurs, the peak detection circuit may be configured to isolate the delicate circuitry of the analog front end of the transmitter unit from the power supply, and rather allow the electrometer and the analog front end circuitry of the transmitter to draw the necessary power from a capacitor of the peak detection circuit to ensure continuous and proper operation.

Accordingly, in accordance with the various embodiments of the present invention, by using a peak detection circuit with a tuned low pass filter, an effective, low cost and low noise approach to isolating the battery droop, even that in excess of 0.5 volts, may be achieved such that in the monitoring system discussed above, the detected and processed data values are not substantially effected, and the delicate analog circuitry of the transmitter is not adversely effected by the fluctuation in power supply signal.

Various other modifications and alterations in the structure and method of operation of this invention will be apparent to those skilled in the art without departing from the scope and spirit of the invention. Although the invention has been described in connection with specific preferred embodiments, it should be understood that the invention as claimed should not be unduly limited to such specific embodiments. It is intended that the following claims define the scope of the present invention and that structures and methods within the scope of these claims and their equivalents be covered thereby.

What is claimed is:

1. An analyte monitoring system, comprising:
    an analyte sensor at least a portion of which is configured to be in fluid contact with an analyte, the analyte sensor configured to detect an analyte level;
    a transmitter unit including an analog interface operatively coupled to the analyte sensor and configured to receive one or more signals associated with the analyte level, the transmitter unit configured to transmit one or more data corresponding to the one or more signals associated with the analyte level, the transmitter unit further including a peak detection unit configured to detect a condition associated with a power source of the transmitter unit, the peak detection unit configured to electrically isolate the power source of the transmitter from the analog interface when the condition is detected; and
    a receiver unit configured to receive the one or more data corresponding to the one or more signals associated with the analyte level from the transmitter unit when the condition associated with the power source of the transmitter unit is detected;
        wherein the analog interface is configured to draw power from the peak detection circuit when the condition associated with the power source is detected and is isolated from the power source.

2. The system of claim 1 wherein the receiver unit includes a display unit for displaying data associated with the received one or more signals associated with the analyte level.

3. The system of claim 1 wherein the peak detection circuit includes:
    a diode including an input terminal and an output terminal said input terminal of said diode configured to receive an input signal;
    a capacitor operatively coupled to said output terminal of said diode; and
    an output terminal operatively coupled to said capacitor and said output terminal of said diode for outputting an output signal.

4. The system of claim 3 wherein said diode includes a Schottky diode switch.

5. The system of claim 3 wherein said input signal includes a voltage signal from a power supply.

6. The system of claim 3 wherein the detected condition includes a voltage droop associated with the power source.

7. The system of claim 6 wherein the voltage droop is detected at said input terminal of said diode, and further, wherein said diode and said capacitor are configured to compensate for said voltage droop.

8. The system of claim 1 wherein the detected condition is associated with the transmission of the one or more data corresponding to the one or more signals associated with the analyte level.

9. The system of claim 1 wherein the analyte sensor includes a glucose sensor.

10. The system of claim 1 wherein the analyte sensor includes an electrochemical sensor.

11. A data communication system, comprising:
    an analyte sensor at least a portion of which is configured to be in fluid contact with an analyte, the analyte sensor configured to detect an analyte level;
    a transmitter unit including an analog interface operatively coupled to the analyte sensor and configured to receive one or more signals associated with the analyte level, the transmitter unit configured to transmit one or more data corresponding to the one or more signals associated with the analyte level, the transmitter unit including:
        a peak detection circuit configured to receive the power supply signal, and further to output a detected signal; and
        a low pass filter operatively coupled to said detection circuit, said low pass filter configured to receive said detected signal;

wherein said peak detection circuit is configured to detect a voltage droop in said power supply signal during transmission of the one or more data corresponding to the one or more signals associated with the analyte level, and further configured to electrically isolate the analog interface from the power supply signal; and a receiver unit configured to receive the one or more data corresponding to the one or more signals associated with the analyte level from the transmitter unit;

wherein when the analog interface is electrically isolated from the power supply signal, the analog interface of the transmitter unit is configured to draw power from the peak detection circuit.

12. The system of claim 11 wherein said peak detection circuit includes a passive switching configuration.

13. The system of claim 11 wherein said peak detection circuit includes a diode operatively coupled to a capacitance.

14. The system of claim 13 wherein said diode includes a Schottky diode switch.

15. The system of claim 11 wherein the receiver unit includes a display unit for displaying data associated with the received one or more signals associated with the analyte level.

16. A method of monitoring data, comprising the steps of:
positioning an analyte sensor in fluid contact with an analyte;
detecting an analyte level from the analyte sensor;
transmitting one or more signals associated with the detected analyte level from the analyte sensor received by an analog interface of a data transmitter;
detecting a predetermined condition related to a power source; and
electrically isolating the analog interface from the power source when the predetermined condition is detected; and
supplying power to the analog interface from a source other than the power source when the predetermined condition is detected and the analog interface is electrically isolated from the power source;
wherein the one or more signals associated with the detected analyte level from the analyte sensor are transmitted during the time period when the predetermined condition is detected.

17. The method of claim 16 further including the step of receiving the transmitted one or more signals associated with the analyte level.

18. The method of claim 16 wherein transmitting includes:
providing a diode having an input terminal and an output terminal said input terminal of said diode configured to receive an input signal;

operatively coupling a capacitor to said output terminal of said diode; and
operatively coupling an output terminal to said capacitor and said output terminal of said diode for outputting an output signal.

19. The method of claim 18 wherein said diode includes a Schottky diode switch.

20. The method of claim 18 wherein said input signal includes a voltage signal from a power supply.

21. The method of claim 18 further including the steps of:
detecting a voltage droop at said input terminal of said diode, and
compensating for said voltage droop by said diode and said capacitor.

22. The method of claim 16 wherein the detected condition includes voltage droop associated with the power source.

23. The method of claim 16 wherein the analog interface is electrically coupled to the power source when the predetermined condition is no longer detected.

24. The method of claim 16 wherein the predetermined condition is detected during transmission of the one or more signals associated with the detected analyte level.

25. A method of providing peak detection in a data communication system, comprising the steps of:
positioning an analyte sensor in fluid contact with an analyte;
detecting an analyte level from the analyte sensor;
receiving one or more signals associated with the detected analyte level at an analog interface of a data transmitter operatively coupled to the analyte sensor;
configuring a peak detection circuit of the data transmitter to detect a voltage droop in a power supply signal, to electrically isolate the analog interface from the power supply signal, and to output a compensated signal;
low pass filtering said compensated signal from said peak detection circuit; and
transmitting the one or more signals associated with the analyte level or the low pass filtered compensated signal over a data network;
wherein when the analog interface is electrically isolated from the power supply signal, the analog interface of the transmitter unit is configured to draw power from the peak detection circuit.

26. The method of claim 25 wherein said step of providing said peak detection circuit includes providing a passive switching configuration.

27. The method of claim 25 wherein said step of configuring said peak detection circuit includes the step of operatively coupling a diode to a capacitance.

* * * * *